United States Patent
Weber et al.

(10) Patent No.: US 10,391,421 B2
(45) Date of Patent: Aug. 27, 2019

(54) TEMPERATURE-ASSISTED ON-COLUMN FOCUSING

(71) Applicant: University of Pittsburgh—of the Commonwealth System of Higher Education, Pittsburgh, PA (US)

(72) Inventors: Stephen Weber, Allison Park, PA (US); Stephen Robert Groskreutz, Homestead, PA (US); Anthony Robert Horner, Pittsburgh, PA (US); Rachael-Anh Elizabeth Wilson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 561 days.

(21) Appl. No.: 14/996,104

(22) Filed: Jan. 14, 2016

(65) Prior Publication Data

US 2016/0206971 A1    Jul. 21, 2016

Related U.S. Application Data

(60) Provisional application No. 62/104,548, filed on Jan. 16, 2015.

(51) Int. Cl.
*B01D 15/16*    (2006.01)
*B01D 15/18*    (2006.01)
(Continued)

(52) U.S. Cl.
CPC .......... *B01D 15/161* (2013.01); *B01D 15/16* (2013.01); *B01D 15/18* (2013.01);
(Continued)

(58) Field of Classification Search
CPC ...... B01D 15/16; B01D 15/161; B01D 15/22; B01D 15/1871; B01D 15/424;
(Continued)

(56) References Cited

U.S. PATENT DOCUMENTS

| | | | | |
|---|---|---|---|---|
| 3,719,084 A | * | 3/1973 | Walker | G01N 30/461 73/23.25 |
| 2007/0144971 A1 | * | 6/2007 | Bonn | B01J 20/261 210/656 |

(Continued)

FOREIGN PATENT DOCUMENTS

WO    WO 2010/057826    5/2010

OTHER PUBLICATIONS

Collins, D., et al., "Versatile capillary column temperature control using a thermoelectric array based platform", Analytical Chemistry, 83, 4307-4313 (2011).*

(Continued)

*Primary Examiner* — Benjamin L Lebron
(74) *Attorney, Agent, or Firm* — Klarquist Sparkman, LLP

(57) ABSTRACT

A method of comprising:
introducing a sample volume into an inlet end of a liquid chromatography column, wherein the liquid chromatography column includes a focusing segment proximal to the inlet end of the liquid chromatography column and a separation segment proximal to an elute outlet of the liquid chromatography column;
maintaining only the focusing segment at a first temperature as the sample is introduced into the focusing segment; and
subsequently heating the focusing segment to a second temperature that is higher than the first temperature after the entire sample volume has been introduced into the focusing segment.

17 Claims, 24 Drawing Sheets

(51) Int. Cl.
*B01D 15/20* (2006.01)
*G01N 30/30* (2006.01)
*G01N 30/60* (2006.01)
*G01N 30/02* (2006.01)
*G01N 30/16* (2006.01)
*B01D 15/32* (2006.01)
*B01D 15/30* (2006.01)

(52) U.S. Cl.
CPC ..... *B01D 15/1864* (2013.01); *B01D 15/1871* (2013.01); *B01D 15/206* (2013.01); *G01N 30/30* (2013.01); *G01N 30/6039* (2013.01); *B01D 15/305* (2013.01); *B01D 15/325* (2013.01); *G01N 2030/027* (2013.01); *G01N 2030/167* (2013.01); *G01N 2030/303* (2013.01); *G01N 2030/3046* (2013.01); *G01N 2030/3053* (2013.01)

(58) Field of Classification Search
CPC .. B01D 15/206; B01D 15/168; B01D 15/325; B01D 15/305; B01D 15/18; B01D 15/1864; G01N 30/30; G01N 30/6039; G01N 30/6095; G01N 30/606; G01N 30/6091; G01N 30/461; G01N 30/7233; G01N 30/7266; G01N 30/08; G01N 30/56; G01N 2030/027; G01N 2030/167; G01N 2030/303; G01N 2030/3046; G01N 2030/8881; G01N 2030/3015; G01N 2030/3076; G01N 2030/122; G01N 2030/3053; G01N 2030/3007; G01N 2030/8831; G01N 2030/565; G01N 2030/562; B01L 3/502715; B01L 2200/028; B01L 2200/027; B01L 2200/025; B01L 2400/0487; B01L 2300/0816; B01J 20/283
See application file for complete search history.

(56) References Cited

U.S. PATENT DOCUMENTS

2009/0173146 A1* 7/2009 Pursch ................ G01N 30/30
73/61.52
2011/0252873 A1* 10/2011 Vorm ..................... G01N 30/08
73/61.53
2012/0171773 A1* 7/2012 Murphy ............ B01L 3/502715
436/86
2013/0193051 A1* 8/2013 Wirth ..................... G01N 30/56
210/198.2

OTHER PUBLICATIONS

Woonton, B.W. and G.W. Smithers. (2010). "Novel adsorbents and approaches for nutraceutical separation". In S.S.H. Rizvi (Eds.), Separation, Extraction and Concentration Processes in the Food, Beverage, and Nutraceutical Industries (pp. 148-179). Elsevier Science & Technology.*
Guiochon, G., "Monolithic columns in high-performance liquid chromatography", Journal of Chromatography A, 1168, pp. 101-168 2007).*
Contreras et al., "Dynamic thermal gas gradient chromatography," *Journal of Chromatography A*, No. 1302, pp. 143-151, Jun. 14, 2013.
Contreras et al., "Peak sweeping and gating using thermal gradient gas chromatography," *Journal of Chromatography A*, No. 1278, pp. 160-165, Jan. 9, 2013.
Eghbali et al., "Exploring the Possibilities of Cryogenic Cooling in Liquid Chromatography for Biological Applications: A Proof of Principle," *Analytical Chemistry*, No. 84, pp. 2031-2037, Jan. 17, 2012.
Groskreutz et al., "Temperature-assited on-column solute focusing: A general method to reduce pre-column dispersion in capillary high performance liquid chromatography," *Journal of Chromatography A*, No. 1354, pp. 65-74, May 28, 2014.
Holm et al., "Novel column oven concept for cold spot large volume sample enrichment in high throughput temperature gradient capillary liquid chromatography," *J. Sep. Sci.*, No. 26, pp. 1147-1153, Jan. 8, 2003.
Molander et al., "Temperature-Programmed Packed Capillary Liquid Chromatography Separation with Large Volume On-Column Focusing Retinyl Esters," *J. High Resol. Chromatogr.*, 22(9):490-494, Sep. 1999.
Molander, et al., "Temperature-promoted large-volume solute enrichment in column-switching miniaturized liquid chromatography," *Analyst*, No. 127, pp. 892-897, Jun. 10, 2002.

* cited by examiner

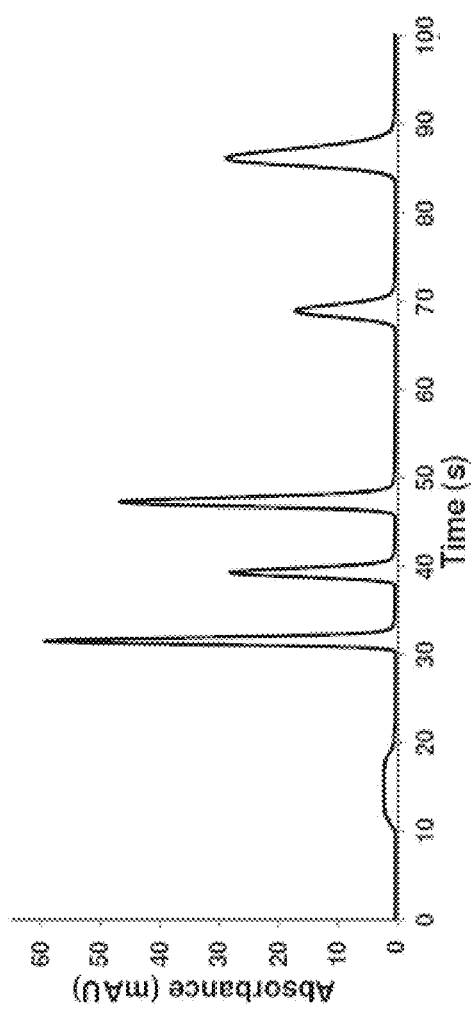
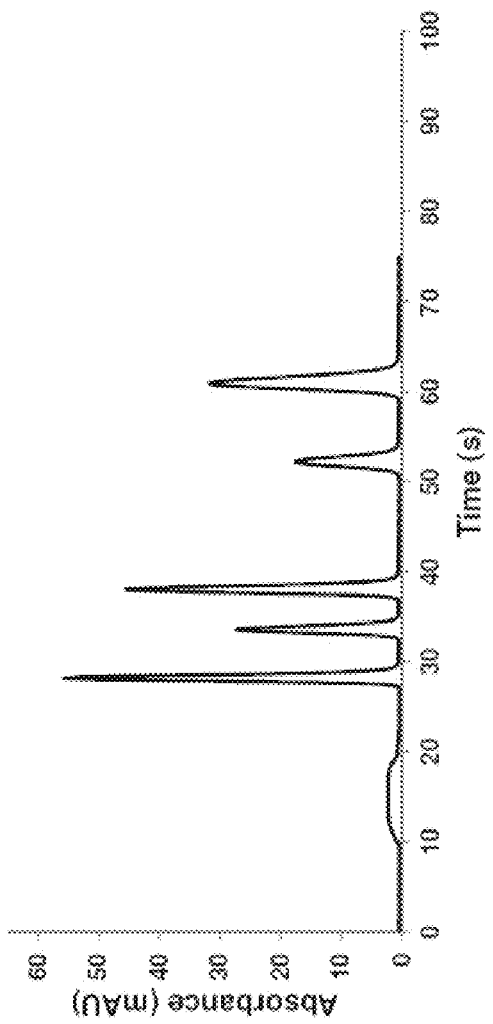
FIG. 12A
FIG. 12B

TEMPERATURE-ASSISTED ON-COLUMN FOCUSING

This application claims the benefit of U.S. Provisional Appl. No. 62/104,548, fild Jan. 16, 2015, which is incorporated herein by reference in its entirety.

ACKNOWLEDGMENT OF GOVERNMENT SUPPORT

This invention was made with government support under grant numbers GM044082 and MH104386 awarded by the National Institutes of Health. The government has certain rights in the invention.

BACKGROUND

Liquid chromatography (LC) columns have been extensively developed and are used routinely in both analytical and preparative chromatography. The separation in a chromatography column of a sample comprising a mixture of components (also termed analytes or solutes) is achieved by dissolving the sample if it is solid in a liquid and injecting the sample into a flowing stream of mobile phase. The sample may be a liquid in which case dilution with another liquid prior to injection is optional. The components of the sample are carried through a tubular column where they may interact with the stationary phase typically packed within, thereby causing the sample to separate into its components due to different partitioning between the mobile and stationary phases of the different components (i.e. the components have different partition coefficients). In liquid chromatography the stationary phase is typically in the form of a bed of particles packed within the column.

The primary advantage of LC stems from its ability to separate, determine the concentration of and identify (with suitable means) 60-80% of all existing compounds. Column liquid chromatography is the most commonly used type of LC. The separation of components of a mixture as the mixture passes through the column is based on each type of chemical constituent having a unique velocity. The velocity of a constituent depends on its partitioning between the moving liquid passing through the column and the particles that make up the so-called packed bed in the column. In column chromatography when an analytical measurement is the objective, e.g. measure component concentrations or determine what components are present, a sample with a volume much smaller than the column volume is introduced to the column. The sample when first introduced into the column thus occupies a small zone containing all of its components at the head or top of the column. As the separation proceeds, the components separate based on differences in partitioning, but the zones also spread due to a number of processes occurring within the column that are well-known to one of skill in the art. A separation is better when these natural spreading processes are minimized. The recent significant improvements in particle technology (i.e. sub-2 μm fully porous and core-shell particles) provide scientists with better separations by minimizing the natural spreading process.

Small volume samples are commonly encountered in the fields of metabolomics, proteomics, forensics, neurochemistry and single cell analysis. The high complexity and mass limited nature of such small samples requires the column to have a small diameter to limit sample dilution. On the other hand, injecting a volume that is too small leads to difficulty in making quantitative measurements because the components are dilute at the time they are detected leading to a low analytical signal. Injecting a volume that is too large makes the initial zone on the top of the column wider, adding to the natural spreading occurring on column, making the separation worse. The latter problem is called volume overload. In many critical applications, the range of allowable injection volumes is small. The injection volume must be large enough to provide an adequate signal and be small enough to avoid significantly increasing the spreading of the zones.

SUMMARY

Disclosed herein is a method of comprising:
introducing a sample volume into an inlet end of a liquid chromatography column, wherein the liquid chromatography column includes a focusing segment proximal to the inlet end of the liquid chromatography column and a separation segment proximal to an elute outlet of the liquid chromatography column;
maintaining only the focusing segment at a first temperature as the sample is introduced into the focusing segment; and
subsequently heating the focusing segment to a second temperature that is higher than the first temperature after the entire sample volume has been introduced into the focusing segment.

Also disclosed herein is a device comprising:
a liquid chromatography column having a longitudinal axial length and including a sample introduction inlet, an elute outlet, a longitudinally-extending focusing segment proximal to the inlet end of the liquid chromatography column, and a longitudinally-extending separation segment proximal to the elute outlet end of the liquid chromatography column, wherein the focusing segment is longitudinally axially adjacent to the separation segment within the liquid chromatography column; and
at least one Peltier thermoelectric cooling element aligned along the focusing segment.

Further disclosed herein is a device comprising:
an elongated body defining an internal annular elongated column having a sample introduction inlet, a sample outlet, and at least one longitudinally-extending focusing segment;
a thermal sheet contiguous with an outer surface of the body;
at least one Peltier thermoelectric cooling element aligned along the at least one focusing segment and contiguous with an outer surface of the thermal sheet; and
a heat sink contiguous with an outer surface of the Peltier thermoelectric cooling element.

Additionally disclosed herein is a device comprising:
a precolumn having a longitudinal axial length and comprising a sample introduction inlet, an elute outlet, at least one longitudinally-extending focusing segment, and at least one Peltier thermoelectric cooling element aligned along the focusing segment; and
a liquid chromatography column coupled to the elute outlet the precolumn, wherein the liquid chromatography column includes a longitudinally-extending separation segment.

Also disclosed herein is a method for modifying a liquid chromatography column comprising coupling to a sample inlet of the liquid chromatography column a precolumn having a longitudinal axial length and comprising a sample introduction inlet, an elute outlet, at least one longitudinally-extending focusing segment, and at least one Peltier thermoelectric cooling element aligned along the focusing segment, wherein the sample inlet of the liquid chromatography column is coupled to the elute outlet of the precolumn.

The foregoing will become more apparent from the following detailed description, which proceeds with reference to the accompanying figures.

BRIEF DESCRIPTION OF THE DRAWINGS

FIG. 4a shows an arrangement in which all three segments are packed with the same particles, which is the least desirable embodiment. FIG. 4b shows an arrangement with segment 2a is void. FIG. 4c shows an arrangement in which segment 2a is packed with different particles compared to segments 2b and 2c. The segments 2a, 2b, and 2c are shown in the order corresponding to the flow direction of a sample. In other words, segment 2b is downstream from segment 2a, and segment 2c is downstream from segment 2b.

FIGS. 12A and 12B are graphs depicting the results of constant pressure LC.

FIG. 14B shows the result of temperature-based focusing and comparative FIG. 14A shows the results of no temperature-based focusing.

FIG. 15B shows the result of temperature-based focusing and comparative FIG. 15A shows the results of no temperature-based focusing.

DETAILED DESCRIPTION

Figure 1:
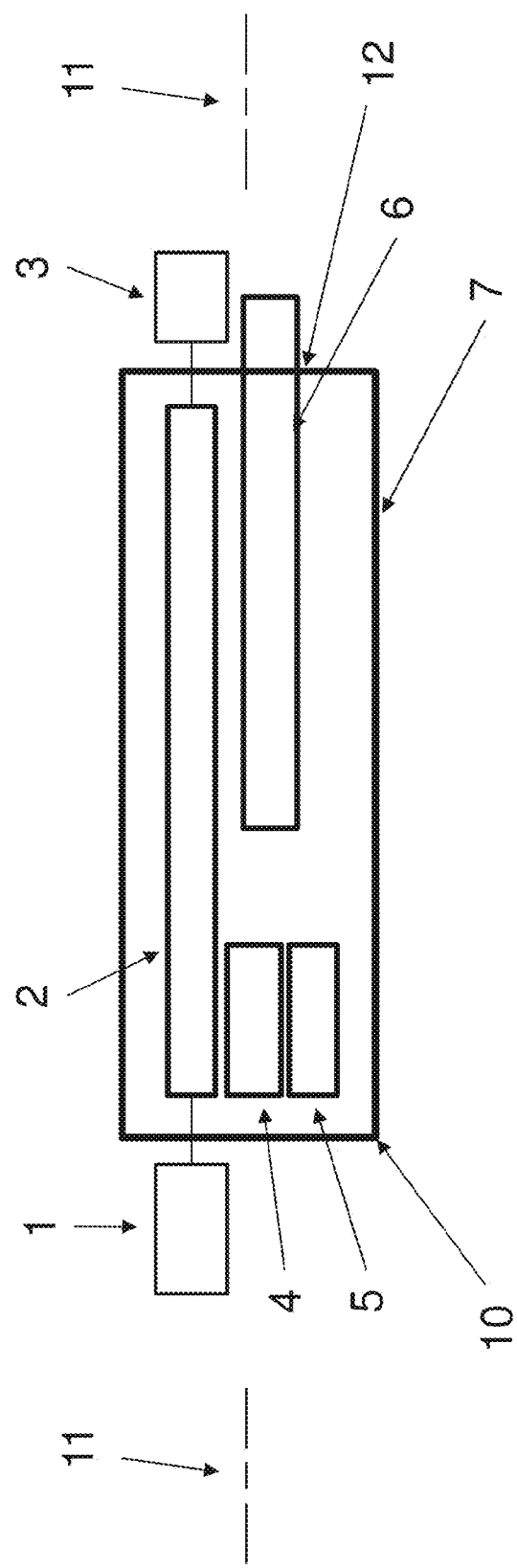
FIGS. 1-3 are schematics of devices according to the present disclosure

Modern LC systems are instruments with electronically controlled pumps, detection systems, and sample introduction systems to take advantage of the separation that occurs on a column. There are many reasons to decreases the size scale of such instruments and columns, among them are the cost of the high purity mobile phase and the cost of discarding used mobile phase (as hazardous waste, VOCs). However, there are limitations. Chief among these is the ability for a down-sized system to handle a "normal-sized sample" or "large-volume" sample.

However, as capillary LC columns are small, the actual volumes referred to may seem small compared to some other reference volume. In "capillary" or "nano" liquid chromatography, column volumes are in the nL to few µL range.

Another limitation preventing the use of smaller columns and generating less waste (VOCs) relates to complex mixtures. For example, it is common to have samples with hundreds of components with a range of velocities (within the column during the separation) spanning one hundred times. The solution to the problem is known as "gradient elution." By changing the mobile phase (more VOC added) during the separation, the slower components start moving faster over time. Because the fast ones are already out of the column, the change does not affect them. However, the apparatus required is cumbersome, expensive ($60 k), and inefficient. The latter refers to the fact that it takes a long time to return to the original conditions so that another sample may be separated.

Chromatographic separation techniques are classified by the scale of columns used to perform the separation. The majority of LC separations are performed using analytical scale columns, i.e. those with internal diameters (ID) between 4.6 and 2.1 mm. Capillary columns made from fused silica have ID between 500 and 5 µm. Column volume calculated from the fluid volume contained within. For packed columns this value is calculated from the volume of the tube times the total porosity of the packed column; for open-tubular columns, column volume is the volume of the tube. Volumes typically range from 0.05 mL to 2.5 mL for analytical columns and from 30 to 0.01 µL for capillary columns. Typical injection volumes for analytical columns range from 5 to 1 μL, respectively, and from 1000 to 50 nL for capillary columns. To achieve efficient separations the volume of sample, $V_{inj}$, introduced or "injected" onto the column must be small relative to the column volume, $V_{col}$, typically less than 1% of the column volume. Due to the reduced column volumes of capillary columns, for example if $V_{col}$=0.25 μL, then the sample volume should be less than 2.5 nL. This is not possible based on current technology.

Disclosed herein in certain embodiments are temperature-based methodologies addressing the sample introduction problem in capillary LC and capillary LC's current limitations regarding high speed analyses. These methodologies are generally referred to herein as temperature assisted-solute focusing (TASF).

It has been found that cooling a short portion of a capillary column effectively slows down the velocities of constituents with affinity for the stationary phase. The components in an injected volume that would ordinarily create volume overload stick to the column during the injection process, concentrating them into a smaller, acceptable volume on the column.

In certain embodiments cooling and heating can be used on the whole or substantial length of the column to alter constituent velocities rapidly and reversibly, permitting efficiency and flexibility in separations using capillary columns.

According to the methods disclosed herein, a focusing segment of the column proximal to a sample injection end of the column is cooled during injection of a sample. In certain embodiments, the focusing segment is pre-cooled to a desired temperature prior to sample injection. In certain embodiments, the focusing segment is then heated after the cooling once the sample is sufficiently focused. Typically, heating of the focusing segment is initiated after all of the sample resides within the focusing segment. The time at which the focusing segment is heated to a temperature sufficient to perform the separation is dictated by the sample volume, flow rate, and volume of liquid in the column from the outlet of the injection means (typically a loop injector/valve) to the downstream end of the focusing segment. All of the injected liquid must pass into the focusing segment prior to increasing the temperature.

FIGS. 1-4 show illustrative devices that include an LC column 2 having a longitudinal axis 11 and a longitudinally-extending focusing segment 2b proximally located at, or near, an inlet end 10 of the LC column 2. The LC column 2 also includes a longitudinally-extending separation segment 2c proximally located at, or near, an elution end 12 of the LC column 2. In certain embodiments, the focusing segment 2b and the separation segment 2c are longitudinally aligned adjacent to each other along the longitudinal axis 11.

The device optionally includes an inlet segment 2a that is located adjacent to the inlet end 10 of the LC column 2 and aligned along the longitudinal axis 11. The inlet segment 2a may or may not be packed with noninteracting, nonporous silica spheres or other noninteracting material. These particles are present to minimize the empty volume in the column upstream of the focusing segment. They are preferably somewhat larger in diameter than the particles comprising the packed chromatographic bed (i.e., the particles in the focusing segment 2b and separation segment 2c) to minimize the loss of pressure suffered as mobile phase passes through the inlet segment 2a. In certain embodiments, the particle diameter of the particles in inlet segment 2a should be no larger than 10% of the inner diameter of the column. The inlet segment also contains a sample injection valve 1b.

Figure 3:
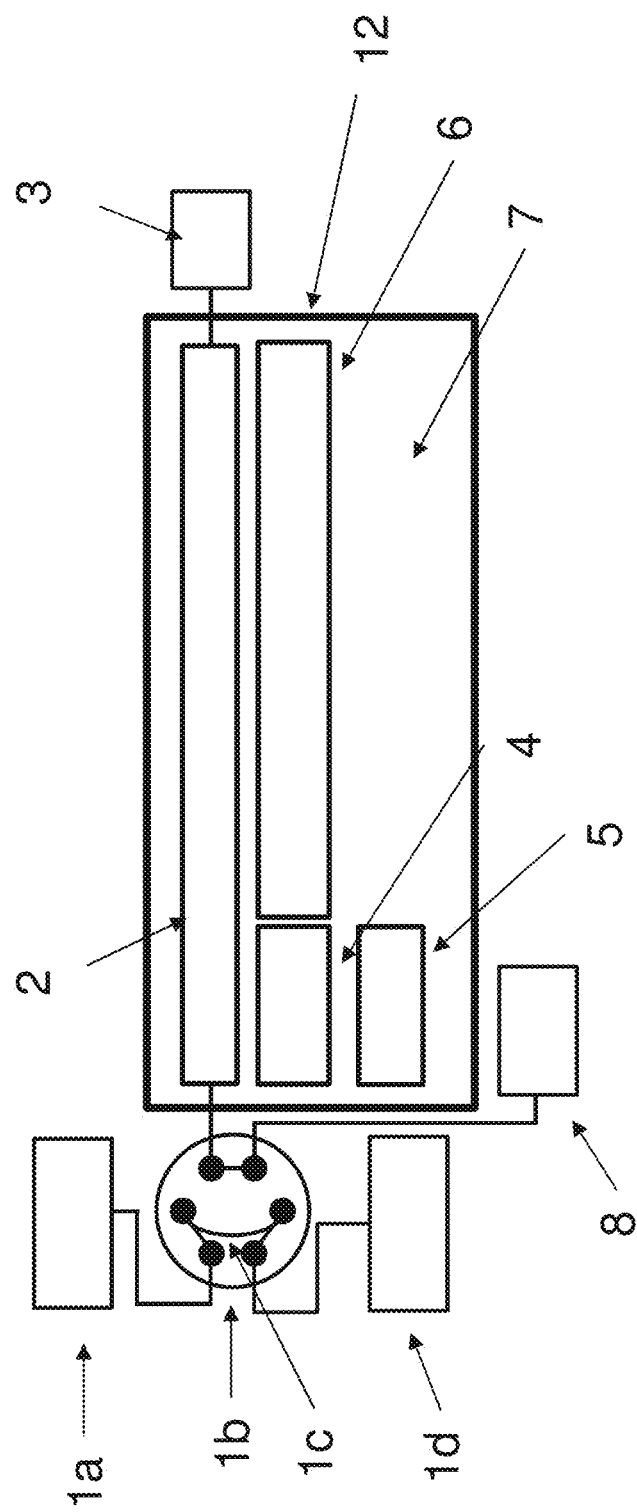
Figure 4:
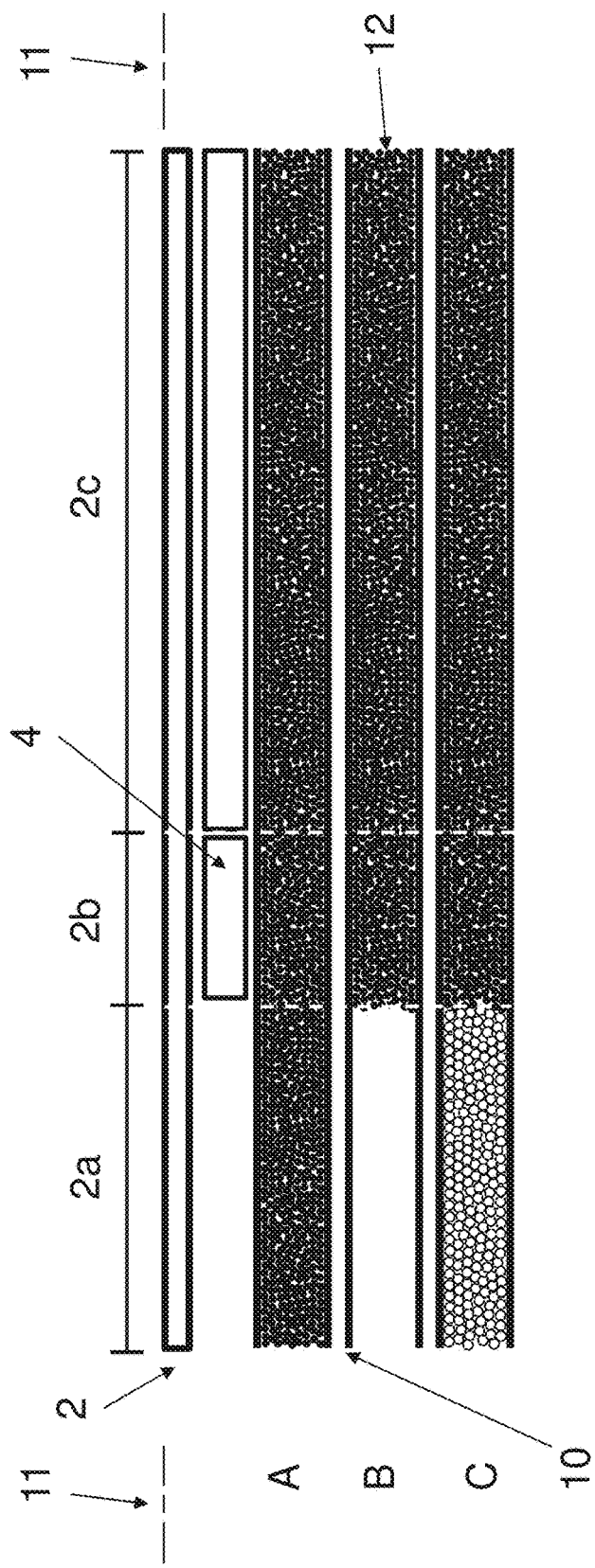
FIG. 4 is a schematic of a device according to the present disclosure (the upper section of FIG. 4) that also shows three possible particle packing arrangements for the segments 2a, 2b and 2c.

As shown in FIG. 3, the device also includes a pump 8 for applying pressure to the mobile phase in the LC column and an associated detector 3 for detecting the eluted component(s) of the sample.

In certain embodiments, the focusing segment has a length that is 1 to 50 percent, more particularly 3 to 35 percent, and most particularly 5 to 20 percent of the total length of the sum of the focusing segment length and the separation segment length. In certain embodiments, the LC column is a capillary column with a length (focusing plus separating segments) of 5 cm and the focusing segment has a length of 0.1 to 1.25 cm, more particularly 0.15 to 1 cm, and most particularly 0.5 to 1 cm.

The focusing segment and the separation segment are packed with stationary phase particles. The particles in the focusing segment may be the same or different compared to the particles in the separation segment. In certain embodiments, the focusing segment may be packed with stationary phase particles that have identical surface chemistry as the particles in the separation segment. In certain embodiments, the focusing segment may be packed with stationary phase particles that have different surface chemistry compared to the particles in the separation segment. In certain embodiments, the focusing segment particles have a larger particle diameter compared to the separation segment particles. For example, the focusing segment particles may have a particle diameter of 1.5 to 10 μm, and the separation segment particles may have a particle diameter of 1.0 to 5 μm. The benefit of larger particles arises from the need for less pressure, however very large particles in the focusing segment will add to the zone spreading occurring from natural process on the separating segment. Thus it is advantageous to use focusing segment particle diameters at least equal in size to those in the separating segment but not more than four times greater than the separation segment average particle diameter. In addition, it may be advantageous to use particles with a different base composition in each segment. Illustrative stationary phase particles for the focusing segment and the separation segment include, for example, zirconia, alumina, or with different surface chemical modifications such as fluorinated phases (e.g., pentafluorophenyl), reversed phases of differing chain lengths, HILIC phases, ion exchange phases, hypercrosslinked phases, carbon based phases and others deemed suitable by one of skill in the art.

The device may also include a heat sink 5 proximately located near a Peltier thermoelectric cooling element (TEC) 4, and a heater 6 (e.g., a resistive heater) aligned along the separation segment. The LC column 2, TEC 4, heat sink 5, and heater 6 may be contained within an insulated enclosure 7.

During operation of the device a sample volume is initially injected via valve 1b into the inlet segment 2a (if present). The sample flows through the inlet segment (there is no sample retention in the inlet segment) and into the inlet end 10 of the focusing segment 2b. The sample is temperature-focused in the focusing segment as described herein. The focused sample then passes through the separation segment in which the component separation occurs.

The focusing segment(s) of the column, or precolumn as described below, is cooled to a temperature ≤30° C. (referred to herein a "first temperature" or "T1") as the sample is introduced into the focusing segment. In certain embodiments, the focusing segment may be cooled to a temperature between than 30° C. to −20° C., more particularly between 20 to −5° C., and most particularly between 10 to 0° C.

In certain embodiments, the focusing period (i.e., the time period at which the focusing segment(s) is maintained at the cooled temperature) can be short, for example <30 s, and equal only to the time required for introduction of the full sample volume into the focusing segment. The exact time value of the focusing segment is sample and application dependent, but the focusing time is selected to be of enough time to load the sample onto the focusing segment 2b without being of a length as to unnecessarily degrade separation performance. The influence of the natural band-spreading processes degrading the separation are increased at the focusing temperature and reduced when focusing segment temperature is increased to match or exceed the separation segment temperature.

After the focusing period, the temperature of the focusing segment(s) is rapidly heated to temperatures ≥T2, for example in about 1000 s or less, more particularly 60 s or less, 20 s or less, and most particularly about 10 s or less, allowing the focused band formed to move more rapidly and enter the separating segment. The differential between the focusing temperature (T1) and the heating temperature (T2) is dependent upon the sample composition and sample size, but generally T2 is at least 20° C. greater than T1, more particularly at least 30° C., and most particularly at least 50° C. In certain embodiments, the heated focusing segment temperature (T2) will be equal to the separating segment temperature. The upper limit of temperature T2 is governed by the particle thermal stability, e.g., 70° C. or 100° C., or 200° C. There is no upper limit to focusing and separation segment temperature based on the TASF process alone.

The cooling of the focusing segment(s) may be accomplished by any means sufficient to achieve desired focusing segment temperature. For example, direct thermoelectric cooling of the column wall may be used to induce focusing. Thermal contact between the column wall and the surface of a Peltier device may be enhanced with a gallium-indium eutectic or similar materials at the interface of the column wall and Peltier. The length of the focusing segment may be defined by the length of the column in contact with the Peltier device.

Figure 2:
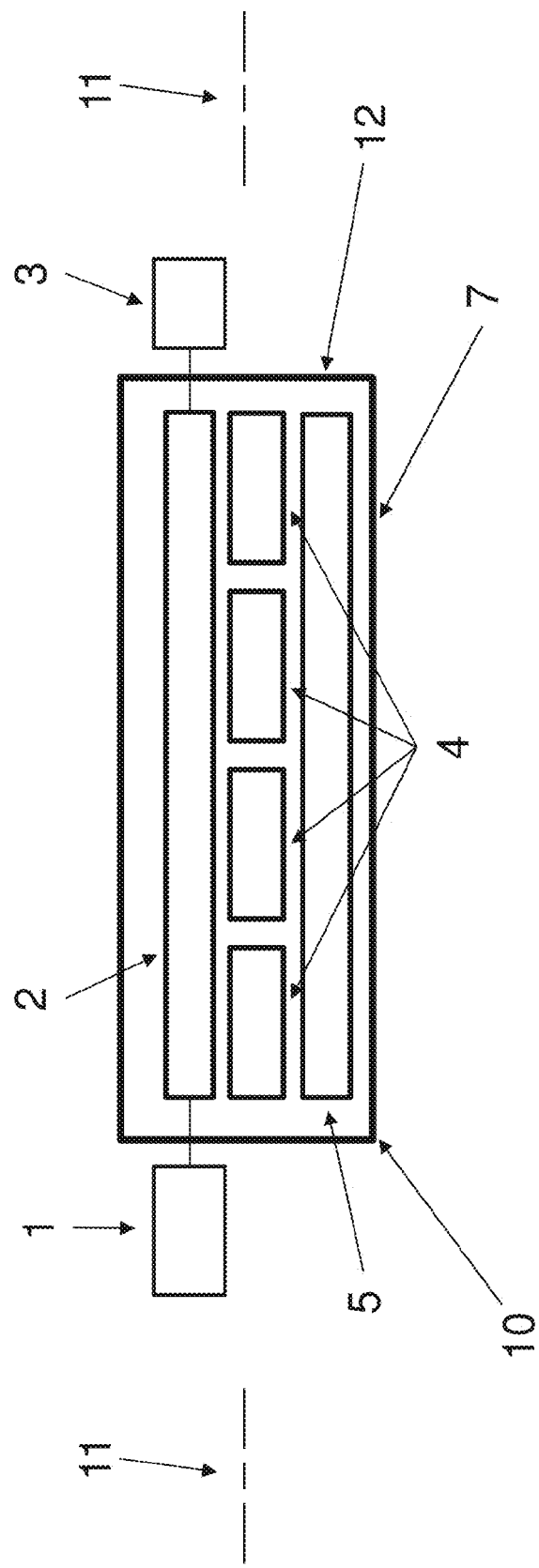
Figure 5:
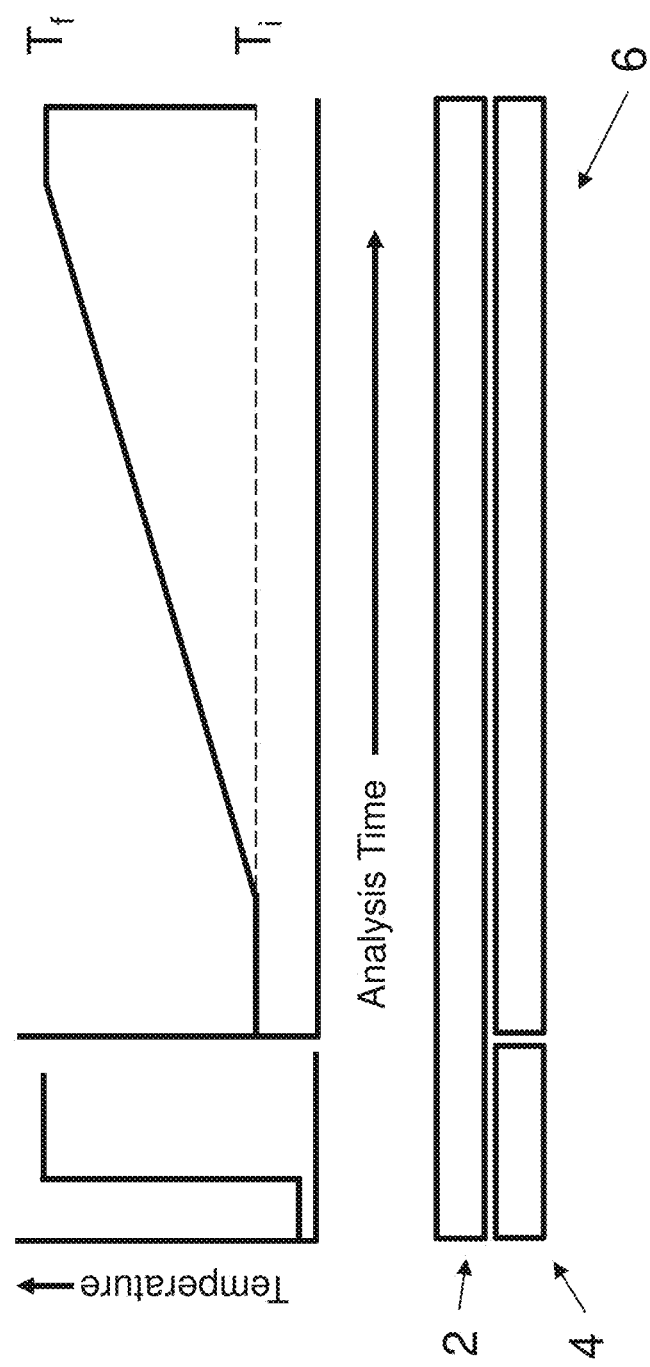
FIG. 5 shows an arrangement in which a device 4 manipulates temperature to focus solutes in the focusing segment 2c as described in FIGS. 1-3. The graph above 4 shows the temperature profile: lower to focus and higher to release. In this embodiment the temperature of segment 2c is not constant during the analysis but starts at temperature $T_i$ and increases with time to temperature $T_f$ as shown in the graph above the separating segment 6.

In certain embodiments, at least one Peltier thermoelectric cooling element (TEC) 4 is positioned adjacent to, and most conveniently under, the focusing segment as shown, for example, in FIG. 1. For instance, linear arrays of independently controlled Peltier elements (TEC) 4 may be aligned along the focusing segment 2b (and optionally along the separation segment) as shown in FIG. 2 to allow implementation of TASF, multiple-stage TASF, and ultrafast temperature programming. Temperature programming refers to changing temperature of the entire column as a function of time. This embodiment depicted in FIG. 5 leverages the rapid heating ability of TECs to quickly heat the separation segment from an initial temperature $T_i$ to a final temperature $T_f$ and more importantly their active cooling capabilities to increase analysis speed by rapidly cooling the column to $T_i$. FIG. 2 depicts a TEC-based instrument capable of performing temperature programming incorporating TASF. In another example, dynamic thermal gradient LC (DTG-LC) is utilized so that the temperature at the outlet of the column is always lower than the inlet. Because the tail end of a constituent band is always at a higher temperature than the front end, the tail is always moving faster than the front, so the zone is continually compressed, improving the separation. For instance, using an array of TECs the column is divided into a series of small (ca. 2 mm) independently temperature-controlled segments. A schematic of the DTG-LC instrument is shown in FIG. 2.

In certain embodiments, the methods and devices disclosed herein increase analysis sensitivity using large volume injections of samples composed of multiple, potentially unknown, low k' solutes to be separated in less than a few minutes (e.g., 3 minutes), or less than one minute.

As used herein, the term "large-volume" refers to the injection volume defined as: the minimum injected volume that increases the observed peak width beyond an acceptable limit such as by 10% of the peak width obtained with a small injection volume compared to the column liquid volume. This volume can be as small as a few percent (e.g., 3 to 7%) of the column volume or as large as a few hundred percent (e.g., 200 to 300%) of the column volume or larger. In liquid chromatography as ordinarily practiced, the volume of a sample introduced or injected into the column is small in comparison to the amount of liquid in the column. The total liquid chromatography column volume is the sum of the fluid volume contained within the focusing segment plus the fluid volume of the separation segment.

In certain embodiments, the method includes transiently cooling the first 1.0 cm of the column to sub-ambient temperatures.

Also disclosed herein are methods to significantly increase the speed and performance of analyses incorporating TASF by operating a chromatographic pump associated with the column at constant pressure throughout the separation rather than in the more commonly used constant flow mode.

Temperature is an important parameter in LC. In addition to influencing solute retention, temperature also influences the pressure required to push mobile phase through the column. The pressure required to create a particular flow rate is directly proportional to mobile phase viscosity. This viscosity decreases as temperature increases. Thus, column pressure at constant flow rate is dependent on column temperature. In addition, the pressure required to maintain a particular flow rate is linearly dependent on the length of the column. In TASF, while a segment of the column is cold during focusing, the mobile phase viscosity is higher than it is in the remaining separation segment. The higher mobile phase viscosity in the focusing segment requires a certain amount of pressure for maintaining a particular mobile phase flow rate. When the focusing segment is returned to the separation temperature, viscosity decreases, and the pressure required to maintain a particular flow rate decreases. In such embodiments, maximum pump pressure is only used during the short sample loading/focusing step, sacrificing speed. This is disadvantageous because the quality (e.g., theoretical plates, theoretical plates per time, separation speed at constant resolution, etc.) of the separation can always be improved by using higher pressure during the separation phase.

In certain novel embodiments disclosed herein constant pressure is applied to the mobile phase during the complete process (i.e. during both cooling/focusing and the heating/separating). The maximum pressure is dependent on the pump used. For example, the constant pressure may be 10 to 5000 bar, more particularly 100 to 2000 bar, and most particularly 200 to 1500 bar. The pressure may be applied via a pump, for example pump 8.

The TASF methods disclosed herein may also be used with solvent-based on-column focusing methods. Solvent-based on-column focusing occurs when injected solute bands are compressed at the head of the column at the separation temperature due to high solute retention while the sample solvent is effectively the mobile phase during the introduction of the sample onto the column. This solvent-based focusing works particularly well for aqueous samples injected into a reversed phase column. TASF acts to increase the focusing effect further. The general principle of focusing is that molecules move in a chromatography column (containing stationary phase) at a velocity that is the mobile phase velocity multiplied by a retardation factor, $R_f$. The numerical value of $R_f$ is less than unity. It is defined by the interaction of a particular solute (component) and the stationary phase and also the mobile phase and the column temperature. The effect of focusing (solvent-based and temperature-based) is to (temporarily) decrease $R_f$. In TASF, temperature is used to focus. If the stationary phases in the focusing and separating zones are the same, and the sample fluid is the mobile phase, then only temperature influences focusing. In the absence of focusing (e.g., with the focusing segment at the column temperature) the $R_f$ of a component will be $R_f(1)$. When the focusing segment is cooled, the retardation factor will decrease, becoming $R_f(2)$. The extent of focusing (the ratio of the zone width without focusing to the zone width with focusing, a number greater than unity) is $R_f(1)/R_f(2)$. For example if $R_f(1)$ is 0.5 and $R_f(2)$ is 0.05, then the use of TASF will compress the injection by a factor of $0.5/0.05=10$ times. If the maximum injection volume without TASF is 50 nL, then under the stated conditions that maximum volume increases to 500 nL. Similarly, for a column at one temperature (no TASF) but with solvent focusing, the retardation factor in the mobile phase will remain $R_f(1)=0.5$, but it will be the smaller value $R_f(3)$ during injection when the injection solvent is the mobile phase. For example, let $R_f(3)$ be 0.1. The compression effect under these conditions is $0.5/0.1=5$. When both TASF and solvent focusing are used, the retardation factor, $R_f(4)$, will be less than either $R_f(2)$ or $R_f(3)$. Therefore, the compression factor when both solvent and temperature-based focusing are used together is $R_f(1)/R_f(4)$ which is greater than the compression for either one alone.

In practice the relative magnitude of compression factors stemming from temperature- and solvent-based focusing or the combination thereof are application dependent. Focusing and retention processes are governed by the specific sample and experimental conditions selected, i.e. the stationary phase used, mobile phase composition, focusing and separation temperatures, are critical to determining the amount of focusing realized. One skilled in the art understands these relationships and the interplay between associated variables. The additional focusing capabilities offered by TASF can be leveraged to improve figures of merit for the specific analytical objective(s).

The combination of solvent-based focusing and temperature-based focusing is easily achieved. For example, many samples are aqueous and the chromatographic mobile phases are mixtures of aqueous solutions or water and organic solvents (e.g., acetonitrile, methanol, ethanol, tetrahydrofuran) used with a reversed-phase stationary phase in the column. These organic solvents are known as "organic modifiers" in the art when used as components of a mobile phase. Solvent based-focusing occurs naturally as the retardation factor is lower in water or aqueous solutions (e.g., buffers) than in aqueous/organic mixtures. Solvent based focusing is not limited to injecting aqueous samples into columns whose mobile phase consists of the aforementioned solvents used for reversed-phase separations. Solvent focusing works for any sample dissolved in solvent systems whose elution strength represents a "weak" eluent, i.e. low retardation factors (high retention) are achieved when using these solvents. Other chromatographic modes benefiting from solvent-based focusing are, but not limited to, normal phase, ion exchange, and hydrophilic interaction liquid chromatography (HILIC). In each operation mode sample compositions can be selected to achieve solvent-based focusing. For example, in HILIC acetonitrile represents a weak eluent, water a strong eluent. Samples consisting of large fractions of acetonitrile benefit from solvent-based focusing. In ion exchange low ionic strength solvents are weak so samples with low ionic strength enhance focusing. Simply using the device described herein effectively combines the focusing abilities of solvent- and temperature-based focusing. As is known in the art, samples that contain strong solvents may be diluted with weak solvents to improve solvent focusing. This procedure is also easily combined with TASF as just described. The only restriction on the combination is to avoid freezing the mobile phase when it is largely aqueous.

TASF may also be used in combination with solvent gradient elution. In liquid chromatography methods that maintain a fixed eluent (mobile phase) composition during the creation of a chromatogram (a "run") are termed isocratic, methods which vary eluent composition as a function of time during the run are termed "gradient elution" or "solvent programming". The latter methods, as known to one of skill in the art, involve changing the eluent composition in a defined way over a period of time so as to generally decrease the solutes' retention. This is typically by means of increasing the organic modifier content. Increasing organic modifier content leads to decreased retention in reversed phase chromatography. Eluents with higher organic modifier content are referred to as being stronger than eluents with less of the same organic modifier content. Decreasing solute retention may be achieved by other means such as changes in surfactant concentration or pH. Gradient elution is widely used in modern liquid chromatography because of its ability to provide efficient separations for samples which contain solutes with a wide range of retentions. One with skill in the art can program a change in eluent composition from a weak to strong eluent to achieve the desired resolution in an acceptable time. For example, in reversed phase LC one initiates the gradient with a low concentration of the organic modifier and during the run increases the concentration of the organic modifier up to a certain composition suited to the task, which is often significantly greater than the initial composition. However, gradient elution is still susceptible to the same injection related bandspreading as isocratic elution, particularly for solutes eluting early in the run. It has been found that TASF improves solvent gradient elution initiated with as little as 5% acetonitrile in a reversed phase separation. As will be recognized by one of skill in the art, the improvement from TASF depends on the particular solutes and conditions at injection.

Figure 16:
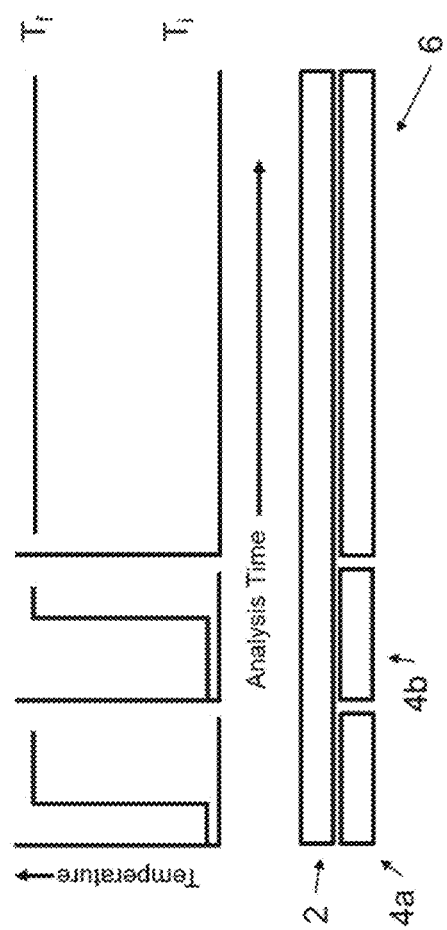
FIG. 16 is a schematic of a two-stage device according to the present disclosure.

According to another embodiment of the TASF method, there are at least two temperature-independent TASF stages or segments. For example, at least two TECS may be arranged longitudinally adjacent to each other in the sample flow direction along the longitudinal length of a LC column. FIG. 16 shows a pair of a first TEC 4a and a second TEC 4b arranged longitudinally adjacent to each other along a LC column 2 to provide two temperature-independent focusing segments. In certain embodiments, a counterpart TEC to TEC 4a may be positioned on the opposite side of the LC column 2, and a counterpart TEC to TEC 4b may be positioned on the opposite side of the LC column 2, to provide a pair of adjacent TECs (i.e., there are four total TECs). Two-stage focusing is realized through introduction of the sample onto the separation column with two cooled TECs 4a and 4b. At a predetermined time (e.g., 5 s) following sample loading, TEC 4a's temperature is increased to release solutes. At this time and for a certain period of time thereafter (e.g., 25 s), TEC 4b's temperature remains cold, thus solute bands are further focused at TEC 4b. After the foregoing certain period of time (e.g., 25 s), TEC 4b is warmed to the separation temperature. Solutes are released from this focusing segment and solutes are separated on the column. This additional focusing segment induces additional focusing.

Applying TASF to larger, commercially available and routinely used liquid chromatography columns is difficult for two reasons. One is that the columns themselves are good conductors of heat so that controlling the temperatures of adjacent segments of the column independently is difficult. In addition, radial temperature gradients in a chromatographic column give rise to bandspreading, decreasing column performance. TASF creates radial temperature gradients in two ways. One way is in space: when the temperature of a segment as controlled from outside the column, e.g., by a TEC or other heating or cooling means, is different from the temperature of the mobile phase coming into that segment, the mobile phase's temperature will change from its preexisting temperature to the new temperature over some distance. That distance is related to the square of the column inside diameter, and so smaller columns permit the mobile phase temperature to reach the appropriate temperature over a much shorter distance than larger columns. There is less bandspreading caused by this effect in smaller columns. A second way for creating radial temperature gradients is in time: when the column temperature is changed, the mobile phase takes time to reach that temperature for reasons similar to those in the preceding statements.

The above-described problems are solved, and the broader application of the TASF approach to larger diameter, more widely used columns is shown as disclosed herein. In particular, the focusing segment should be a physically separate column (referred to herein as "precolumn") from the column used for the separation. In a further embodiment, the heating/cooling means should be sufficient to alter the average mobile phase temperature in the precolumn over the desired range in a few seconds (e.g, 1 to 10 seconds). Disclosed herein is a physically separate TASF precolumn that may be coupled to typical commercially available LC separation columns.

One embodiment of a TASF precolumn is shown in FIGS. 19-23. The TASF precolumn includes a precolumn body 1 that may be made from stainless steel or similar materials. The precolumn body 1 defines an internal annular elongated column 2 that may be packed with stationary phase particles as described above. For instance, a packed column 2 is represented by dashed lines in FIG. 22, which is a longitudinal axial view. The precolumn body 1 has a radial cross-section in a butterfly shape to reduce the mass of the device and increase heat transfer rates within the stainless steel section of the precolumn that defines its focusing segment. In particular, the precolumn body 1 has two triangular portions 20a and 20b that are integral with each other via a central column 21 located at facing apexes of the triangular portions. Thermal sheets 3 that are contiguous with an outer surface of the precolumn body 1 may be provided to improve heat transfer between the precolumn and the heating/cooling elements. In certain embodiments the thermal sheets may be made from 0.004" thick aluminum foil coated on both sides with a non-silicone thermal grease. Heating/cooling elements 4 (e.g., a TEC) are located contiguous with an outer surface of the thermal sheets 3. Heat sinks 5 are located contiguous with an outer surface of the heating/cooling elements 4. Thus, the heating/cooling sub-assembly consists of a thermal sheet:heating/cooling element:heat sink sandwich. Alignment rods 6 are located to hold together the parts of the precolumn. End fittings 7 are provided for coupling the downstream end of the precolumn to an LC separation column and the upstream end of the precolumn to a sample introduction device (e.g, an injection valve).

Figure 23:
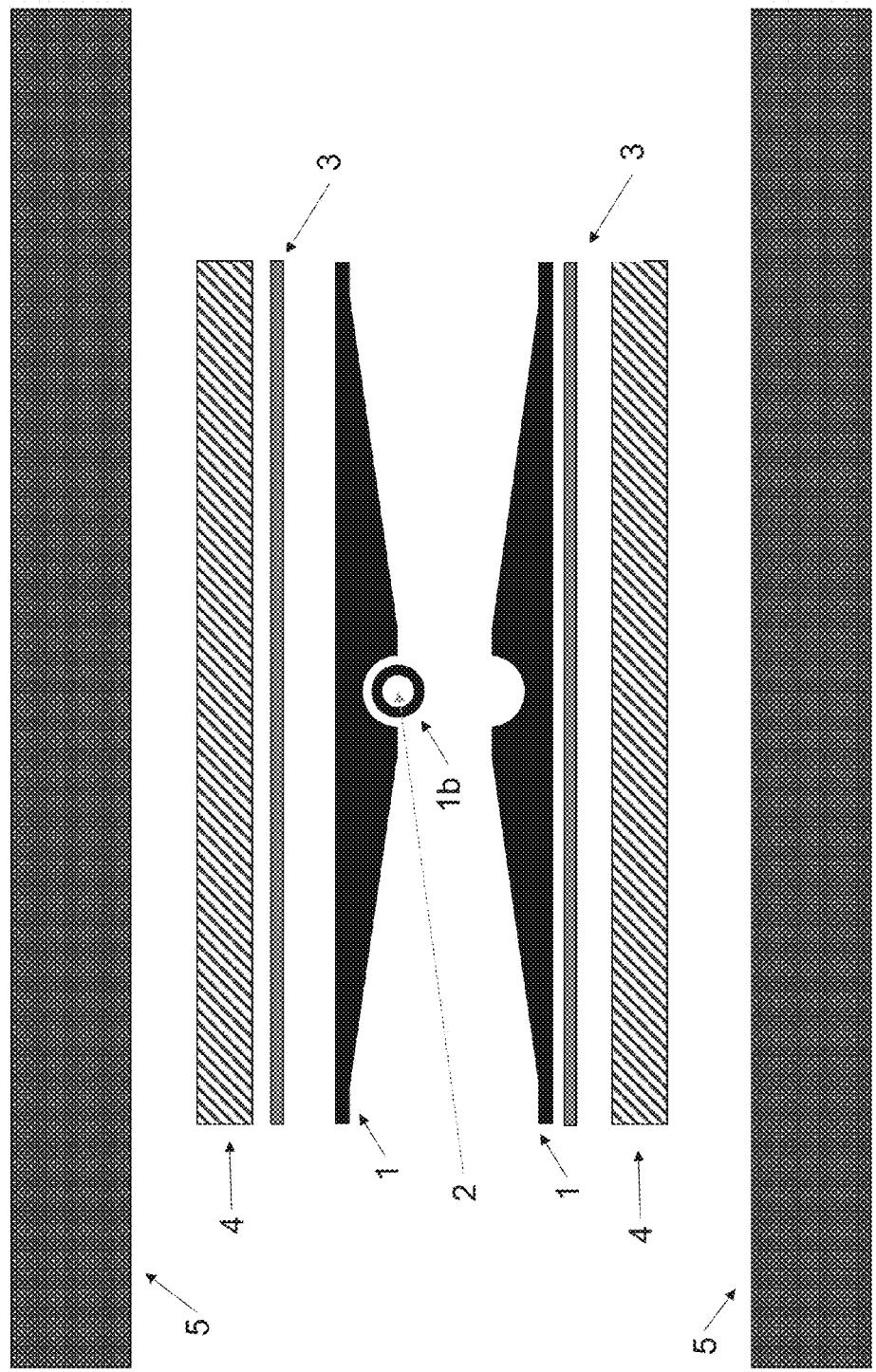
FIG. 23 is a cross-section view of a precolumn that includes a removable column as disclosed herein.

FIG. 23 depicts a precolumn that has a modular design. For example, there may be provided a removable column 1b that can be slidably inserted into a precolumn body. A preexisting column may be fitted with an external precolumn body (e.g., a precolumn body 1 the same or similar to that shown in FIG. 22). In other words, it is not required that the precolumn body and the column be formed from a single machined piece and that each piece could be provided separately in a modular design. Other embodiments of the precolumn may include a different arrangement for the heating/cooling sub-assembly, a different stainless steel precolumn body configuration, and/or other variations. In one embodiment larger internal diameter columns, specifically 1.0 to 4.6 mm ID, more specifically 1.0 to 2.1 mm ID columns can benefit from TASF with large injection volumes, ca. 100 µL. An embodiment of the TASF precolumn consists of a 20 mm long×1.0 mm ID stainless steel column packed with 5 µm stationary phase particles to minimize back pressure in the precolumn. Eight 1.0×1.0 TECs, each capable to delivering 10.9 W of power, are mounted to the surface of the device.

The total power of the TECs and mass of the precolumn have been found to be important factors governing the time required to heat the column following a focusing time. The total mass of the two-cm length of the precolumn is 5.43 g. To heat this mass from an initial focusing temperature of 5° C. to an elution temperature of 70° C. requires 176 J of energy. Heat capacity for stainless steel is 500 $Jkg^{-1}K^{-1}$. The eight 10.9 W TEC can deliver a total of 87.2 W. Thus it takes 2.02 s to warm the precolumn. Had the butterfly or similar reduced mass geometry not been used the mass of the precolumn would increase to 9.53 g increasing the time to 70° C. to 3.58 s. There is a direct relationship between mass of the precolumn and the time required to heat the column. In practice, through numerical simulations using Comsol (5.2) with constant heat flux boundary conditions, it has been find that the actual time taken to bring the center of the column 95% of the way to the goal (67° C.) is 3.4 s. This is mostly due to the fact that heat diffuses axially along the column outside the 2 cm region containing the stationary phase. In certain embodiments, it has been found that 2 to 6 $cm^2$, more particularly 4 $cm^2$ surface contact between the TECs and the column is desirable (a thermal sheet may be interposed between the TEC and column).

Many variations of the particular conditions may be employed to lead to optimum performance. The lengths of the heated and cooled segments may be altered by using TECs of different dimensions (e.g, smaller or larger) or by controlling adjacent TECs in the same way (to obtain the same result as would be obtained from using a larger TEC). With a TASF apparatus designed for the task, e.g., with more than two TECs, more than two stages can obviously be used for increased focusing of selected solutes. For a given arrangement of TECs, the temperatures of the TECs may be controlled in various ways to seek advantageous outcomes. For example, the focusing temperatures of the TECs in multi-stage operations do not need to be the same. The release temperatures of the TECs in multi-stage operation do not need to be the same, nor do they need to be the same as the column temperature.

The methods and devices disclosed herein may be used in any LC application. For example, proteomics is currently driving the development of capillary scale instrumentation. Proteomics is broadly defined as the study of proteins, focusing primarily on their identification, concentration and function within organisms. Most samples analyzed in this field consist of very small volumes (µLs) of protein digest composed of thousands of unique peptide fragments. Following digestion, samples are analyzed using capillary LC coupled to high resolution mass spectrometry. The methods and devices disclosed herein may be used to improve the sample loading process increasing the sensitivity of proteomic separations. The specific problem addressed by TASF is enhanced focusing and subsequent improved identification of early eluting hydrophilic fragments.

In high sensitivity quantitative analysis specific analytes of interest are at or near the detection limits of the detector being used, thus reductions in concentration detection limits are required. This is achieved through increased injection volume; separation performance is maintained using TASF. Other non-proteomic biological applications where sample volume is limited include analysis of blood, serum, plasma, cerebral spinal fluid, etc.

In high speed, routine LC, there is a need for improvement in green analytical chemistry and pharmaceutical applications. In green analytical chemistry the methods and devices leverage the significant savings in solvents/waste by transitioning routine quality control analyses to capillary scale LC. For example, using TASF, conventional 1-5 µL sample volumes can be used with capillary columns rather than the much larger conventional columns.

In pharmaceutical applications the method and devices may be used for dissolution testing in evaluating drug release dynamics. A further application is in impurity profile testing since many pharmaceutical impurities are present at concentrations of orders of magnitude lower than the active pharmaceutical ingredient (API). This necessitates improved sensitivity and detection limits.

In addition, the TASF methods disclosed herein are particularly useful for applications where on-column focusing is required to mitigate volume overload and focus analyte bands, but where sample solvent compositions are fixed and not significantly different from the mobile phase, i.e. where implementation of solvent-based focusing is difficult.

Specific embodiments of the methods and devices are described in the following numbered clauses:

1. A method of comprising:
    introducing a sample volume into an inlet end of a liquid chromatography column, wherein the liquid chromatography column includes a focusing segment proximal to the inlet end of the liquid chromatography column and a separation segment proximal to an elute outlet of the liquid chromatography column;
    maintaining only the focusing segment at a first temperature as the sample is introduced into the focusing segment; and
    subsequently heating the focusing segment to a second temperature that is higher than the first temperature after the entire sample volume has been introduced into the focusing segment.
2. The method of clause 1, further comprising heating the separation segment while cooling the focusing segment.
3. The method of clause 1 or 2, wherein the second temperature is at least 20° C. greater than the first temperature, more particularly at least 30° C. greater than the first temperature, and most particularly at least 50° C. greater than the first temperature.
4. The method of any one of clauses 1 to 3, wherein maintaining the focusing segment at a first temperature comprises cooling the focusing segment for less than 1000 seconds, more particularly 60 seconds or less, and most particularly about 20 seconds or less.
5. The method of clause 1, wherein the separation segment is not cooled.
6. The method of any one of clauses 1 to 5, wherein the liquid chromatography column is a capillary liquid chromatography column.
7. The method of any one of clauses 1 to 6, wherein the total sample volume is at least 50 volume %, more particularly at least 100 volume %, of the total liquid chromatography column volume.
8. The method of any one of clauses 1 to 7, wherein separation of the sample volume is completed in less than three minutes.
9. The method of any one of clauses 1 to 8, wherein the focusing segment contains particles having an average particle diameter that is greater than the average particle diameter of particles contained in the separation segment.
10. The method of any one of clauses 1 to 9, further comprising introducing the sample volume into an inlet segment that is adjacent to the inlet end of the liquid chromatography column prior to introducing the sample volume into the focusing segment.
11. The method of clause 10, wherein the inlet segment contains a sample injection element and noninteracting, nonporous silica spheres.
12. The method of any one of clauses 1 to 11, wherein the focusing segment has a length that is 1 to 50 percent, more particularly 3 to 35 percent, and most particularly 5 to 20 percent, of the total length of the sum of the focusing segment length and the separation segment length.
13. The method of any one of clauses 1 to 12, wherein the sample is associated with a mobile phase and the method further comprises applying a constant pressure to the mobile phase throughout a retention time period of the sample volume in the focusing segment and the separation segment.
14. The method of any one of clauses 1 to 13, further comprising diluting the sample with a weak solvent.
15. The method of any one of clauses 1 to 14, wherein the first temperature is ≤30° C., particularly 30° C. to −20° C., more particularly between 20 to −5° C., and most particularly between 10 to 0° C.
16. A device comprising:
    a liquid chromatography column having a longitudinal axial length and including a sample introduction inlet, an elute outlet, a longitudinally-extending focusing segment proximal to the inlet end of the liquid chromatography column, and a longitudinally-extending separation segment proximal to the elute outlet end of the liquid chromatography column, wherein the focusing segment is longitudinally axially adjacent to the separation segment within the liquid chromatography column; and
    at least one Peltier thermoelectric cooling element aligned along the focusing segment.
17. The device of clause 16, wherein the focusing segment has a longitudinally-extending length that is 1 to 50 percent, more particularly 3 to 35 percent, and most particularly 5 to 20 percent, of the total length of the sum of the focusing segment longitudinally-extending length and the separation segment longitudinally-extending length.

18. The device of clause 16 or 17, wherein the liquid chromatography column is a capillary liquid chromatography column.

19. The device of any one of clauses 16 to 18, wherein the focusing segment contains particles having an average particle diameter that is larger than the average particle diameter of particles contained in the separation segment.

20. The device of any one of clauses 16 to 19, further comprising an inlet segment longitudinally axially adjacent to the inlet end of the liquid chromatography.

21. The device of clause 20, wherein the inlet segment contains a sample injection element and noninteracting, nonporous silica spheres.

EXAMPLES

Example 1

Large Volume Injections with Temperature-based Focusing

Figure 6:
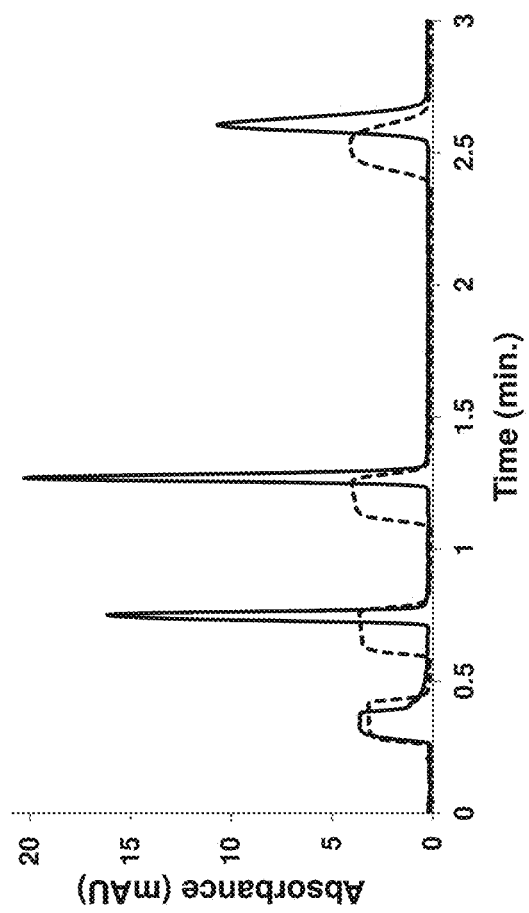
FIG. 6 is a graph depicting the results of a large volume injection with temperature-based focusing.

FIG. 6 shows an overlay for the chromatograms resulting from two injections of 750 nL samples of uracil, methylparaben, ethylparaben and propylparaben under isothermal (dashed line) and TASF (solid line) conditions. (Uracil is a "void volume marker". It does not interact with the stationary phase, it travels through the column substantially in the same way as the mobile phase. As it does not interact significantly, its peak does not become narrower when using TASF or solvent focusing.) Column lengths specified in this and the following examples include the focusing segment and the separating segment, but not the inlet segment. Column dimensions were 47 mm long×0.150 mm ID; the column was packed with Waters BEH C18 particles. Focusing (1.0 cm long) and separation (3.7 cm long) segments were packed with the same diameter, 1.7 μm particles. The inlet segment was 2.5 cm long and packed with 8 μm diameter solid silica spheres. Column volume was estimated to be 450 nL. The sample volume represented an injection 1.65-times the fluid volume of the column. Samples were made to match the elution strength of the mobile phase (sample solvent=mobile phase) to demonstrate the potential for TASF alone to enhance focusing and separation performance for large volumes samples injected onto a high efficiency column. Focusing and separation segment temperatures were 5 and 70° C., respectively. Focusing time was 15 s, and the column flow rate was 4.5 μL/min. After the focusing period of 15 s, the focusing segment temperature was increased to 70° C. Detection was achieved by monitoring absorbance of ultraviolet light at 254 nm. When implementing TASF peak height for retained solutes: methylparaben (peak 2), ethylparaben (3), and propylparaben (4) increased by factors of 4.5, 5.2 and 2.6 relative to the peak height values under isothermal conditions. This simple example clearly shows the potential for TASF to increase peak height, decrease peak width, and improve and separation performance when injecting large volume samples onto capillary columns.

Example 2

Combination of Solvent- and Temperature-based Focusing

Figure 7:
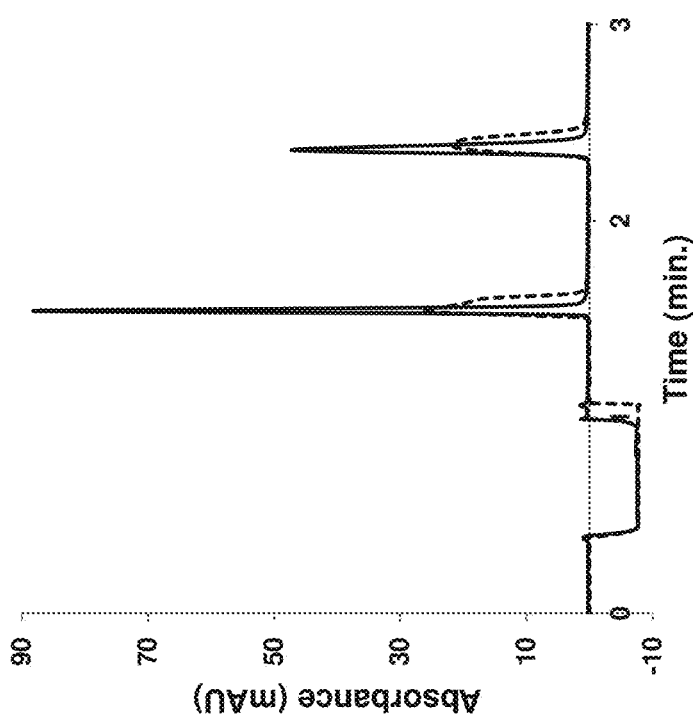
FIG. 7 is a graph depicting the results of a combination of solvent- and temperature-based focusing.

FIG. 7 shows the complementary nature of TASF and the commonly used solvent-based on-column focusing technique. In this example a sample of uracil (unretained void marker), methylparaben and ethylparaben was made in 5% acetonitrile 95% water. Mobile phase composition was set to 20% acetonitrile 80% water and the flow rate was 3 μL/min. Injections of 2 μL samples were made onto the same column described above (example 1) operated under isothermal and TASF conditions. The 2-uL injection represented a volume 4.5-times that of the column. Focusing and separation segment temperatures were −5 and 62.5° C. Focusing segment length was 1.0 cm; focusing time was 45 s. After the focusing period of 45 s, the focusing segment temperature was increased to 62.5° C. Detection was absorbance of UV light at 254 nm. The dashed line trace shows the results for the solvent-based focusing only. The focusing and separation segments were both at 62.5° C., an isothermal experiment. The solid trace demonstrates the improvement from combining solvent focusing and TASF. Peaks are broad due to volume overload due the 2 μL injection even when applying solvent-based focusing. Incorporation of TASF with solvent-based focusing decreased peak widths and increased peak heights. Peak heights increased for methylparaben by a factor of 3.4 and ethylparaben by a factor of 2.2 relative to solvent focusing alone. The combination of both focusing methods is advantageous.

Example 3

High Speed, High Sensitivity LC for Improved Concentration Detection Limits

Figure 8:
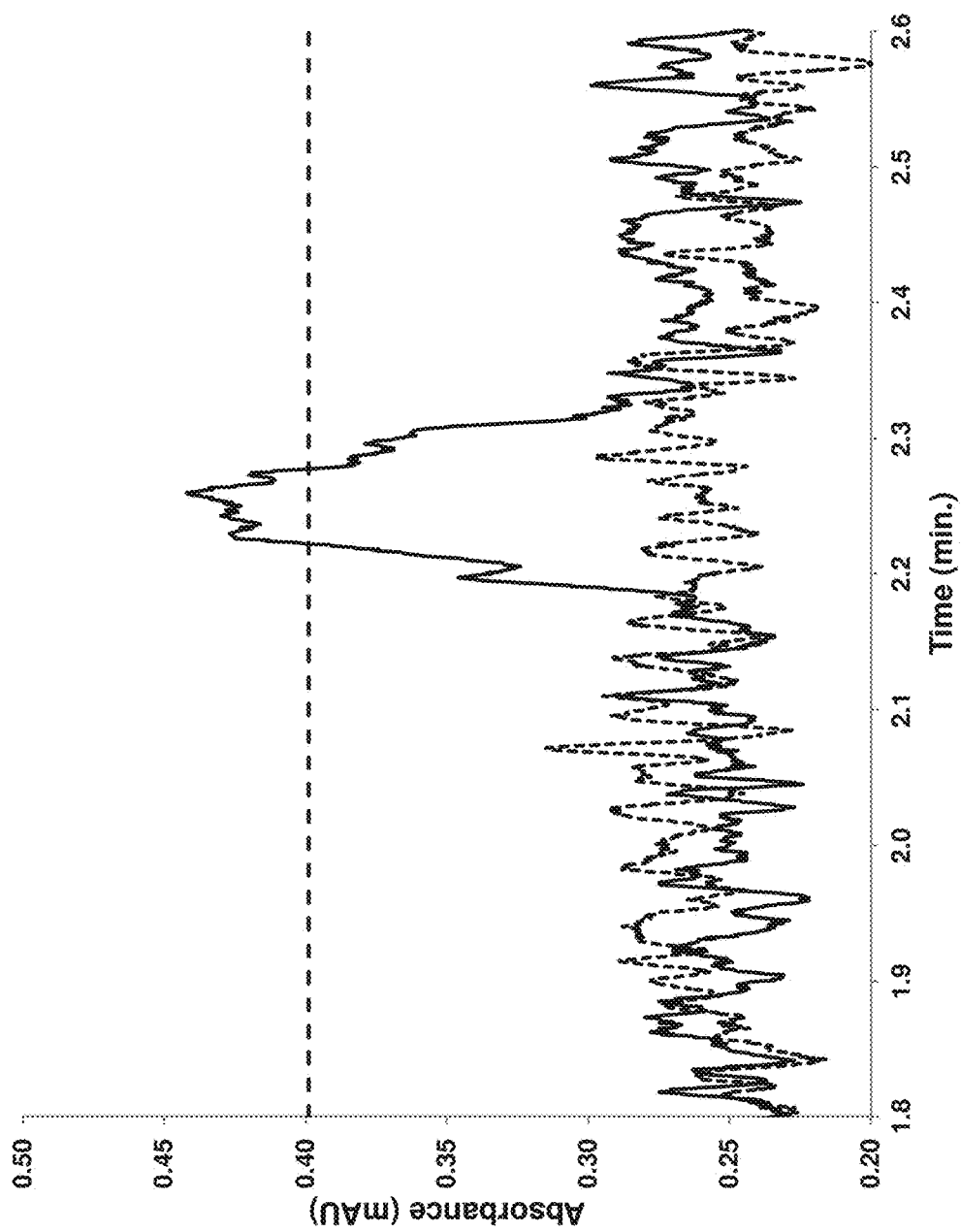
FIGS. 8 and 9 are graphs depicting the results of high speed, high sensitivity LC for improved concentration detection limits.

To assess the practical implementation of TASF the improvements in the concentration detection limits the targeted determination of ethylparaben were evaluated. Assuming constant peak area, reduction in observed peak width due to TASF will result in taller peaks with enhanced signal-to-noise ratios. FIG. 8 demonstrates this potential by comparing 1875 nL injections of ethylparaben under isothermal and TASF conditions. The isothermal separation is shown in dashed line form, TASF in black. Samples were made in made in 20% acetonitrile 80% water and injected onto a 60 mm long×0.150 mm ID Waters BEH C18 column. Separation and focusing segments were packed with 1.7 μm diameter particles. Focusing segment length was 6 mm. The inlet segment was 2.0 cm long and left void as in FIG. 4b. Detection was absorbance of UV light at 220 nm.

Mobile phase composition matched that of the sample. Flow rate was 3 μL/min. Focusing and separation segment temperatures were 5° C. and 60° C., respectively. After the focusing period, the focusing segment temperature was increased to 60° C. What is striking about FIG. 8 comes when comparing the ethylparaben 'peaks' under isothermal and TASF conditions. Subjecting this column to an 1875 nL sample results in no detectable peak present under isothermal conditions. Only using TASF a sample corresponding to nearly 3-times the fluid volume of the column resulted in an easily quantifiable peak above the detector's detection limit (indicated by the dashed line).

Figure 9:
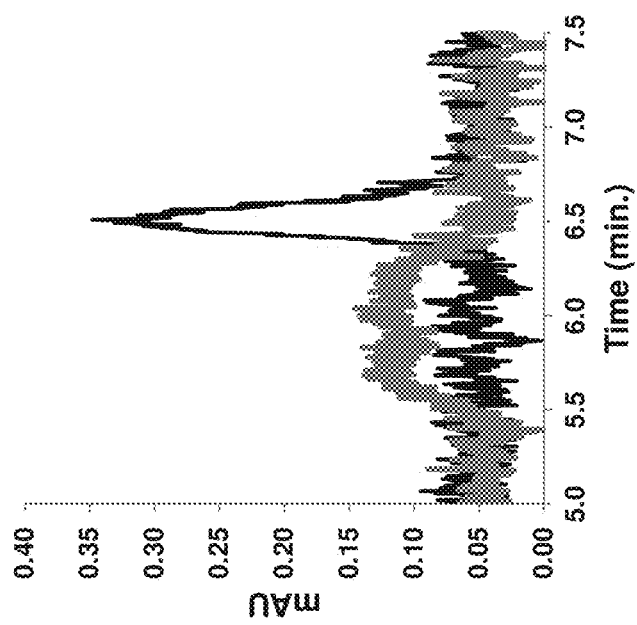

Capillary scale columns are used very often for the analysis of protein and peptide samples. Sample preparation procedures for these solutes often involve the use of large amounts of acetonitrile, e.g. precipitation. Samples contain significant fractions of the organic modifier thereby making them susceptible to volume overload. FIG. 9 shows the analysis of a large volume sample of galanin, a 29 amino acid neuropeptide, dissolved in 20% acetonitrile under isothermal (gray) and TASF (black) conditions. To effectively separate galanin the mobile phase contains 15% acetonitrile and 85% water. Sample volume corresponded to twice the column volume (500 nL) for the 60 mm×0.100 µm ID column packed with Waters CSH C18 particles. Separation and focusing segments were packed with 1.7 µm diameter particles. Focusing segment length was 1.0 cm. The inlet segment was 2.5 cm long and packed with 8 µm diameter solid silica spheres. Detection was absorbance of UV light at 214 nm.

Flow rate was 0.85 µL/min. The isothermal column temperature was 65° C. and the focusing segment temperature was −10° C. The focusing period was 40 s. Clearly the separation has been degraded by volume overload. TASF is shown to improve preconcentration and increase galanin peak height by a factor of 3 relative to the isothermal analysis. This example demonstrates the application of TASF when the injection solvent is stronger than the mobile phase.

Example 4

Fast, High Sensitivity LC

Figures 10A, 10B:
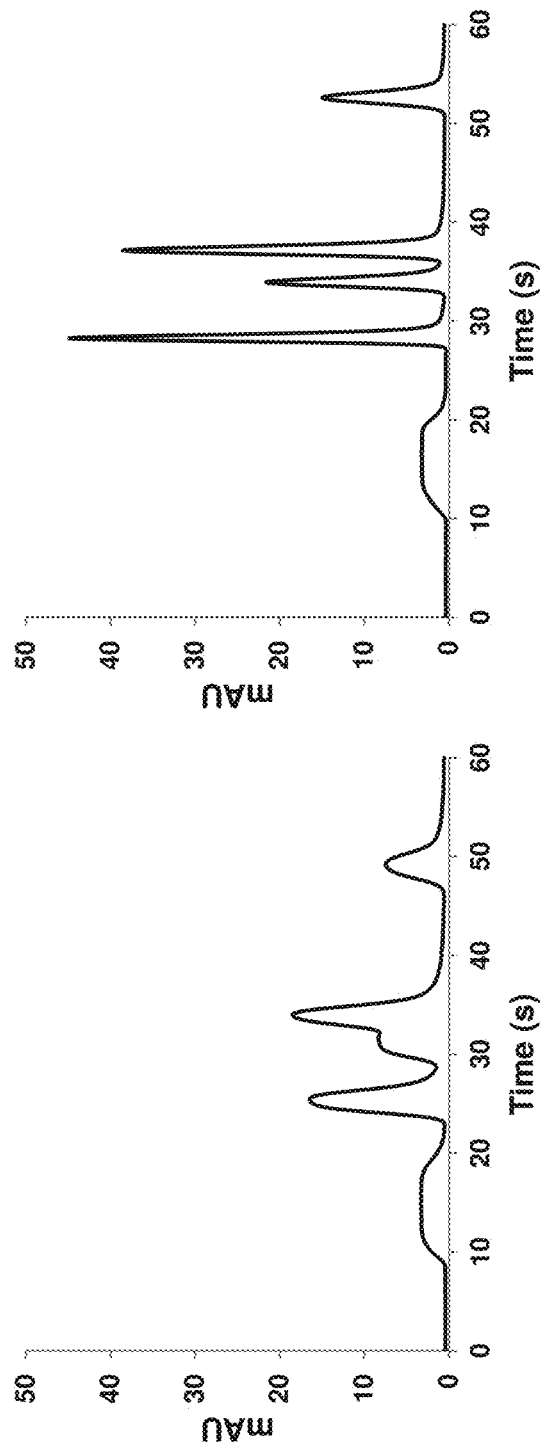
FIGS. 10A and 10B are graphs depicting the results of fast, high sensitivity LC.

High speed LC separations necessitate the use of column temperatures above 60° C. to reduce mobile phase viscosity and increase analyte diffusivity, both attributes that improve separation performance. Unfortunately this increase in performance at temperature compromises capillary columns performance because they are now more susceptible to volume overload. As column temperature is increased the benefits of solvent based focusing are reduced. FIG. 10 demonstrates how TASF can be coupled to fast, high temperature separations to increase analysis speed and sensitivity. Analysis time was fixed at one minute and injection volume at 1 µL. A five component mixture of uracil, parabens and phenones made in 90% water 10% acetonitrile was injected onto a 50 mm long×0.150 mm ID Waters BEH C18 column. Separation and focusing segments were packed with 1.7 µm diameter particles. Focusing segment length was 1.0 cm. The inlet segment was 2.5 cm long and packed with 8 µm diameter solid silica spheres. Detection was absorbance of UV light at 254 nm.

Injection volume to column volume ratio was about two. The mobile phase consisted of 25% acetonitrile 75% water and the flow rate was 7.75 µL/min. Focusing and separation segment temperatures were 5° C. and 80° C. respectively. Focusing time was 15 s; following the separation the focusing segment was reequilibrated to 5° C. at 50 s for the next injection. Panel A of FIG. 10 shows the result from injecting 1 µL of sample onto the column without TASF. This is unacceptable chromatography for quantitative analysis. Panel B shows the TASF trace. Under the conditions sated above implementation of TASF improves analysis sensitivity, i.e. taller peaks, and increases resolution between peaks two through four. This example demonstrates that, despite the fact that TASF takes some time, TASF can be used effectively in fast separations.

Example 5

Constant Pressure

As the viscosity of the mobile phase is higher at lower temperature, it requires more pressure to pump mobile phase during focusing than during the time after focusing when the temperature of the focusing segment has been raised to a higher temperature. As described above, it is advantageous to carry out separations using the maximum pressure capability of the system. For example, with a pump rated to deliver flow at a maximum pressure of 1200 bar a hypothetical 50 mm long×0.15 mm ID column packed with sub-2 um particles can only be operated at 8.3 µL/min when focusing and separation temperatures are 0 and 100° C. (Focusing segment length was 1.0 cm in this calculation.) After focusing, the entire column is heated to 100° C., pressure drops from 1200 bar to 630 bar with constant flow at 8.3 µL/min.

When operating at constant pressure (1200 bar) throughout the analysis the flow rate is still 8.3 µL/min during focusing (with 1 cm of column at 0° C.). After the temperature of this segment is raised to 100° C., the flow rate becomes 15.9 µL/min making better use of the available pump pressure during the entire analysis.

Figure 11B:
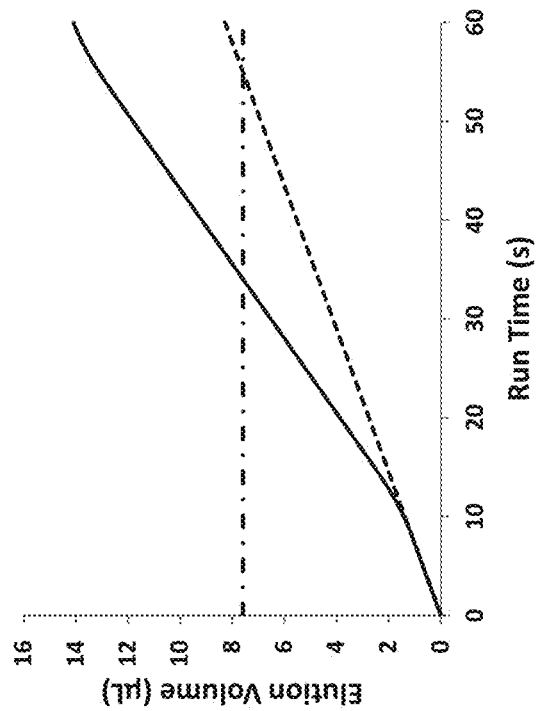
FIGS. 11A and 11B are graphs depicting the results of constant pressure LC.
Figure 11A:
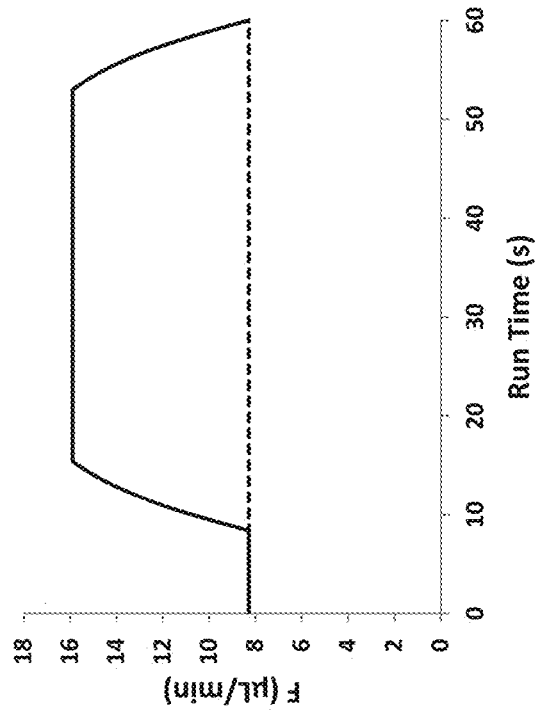

Constant pressure operation is effective for increasing the speed of TASF analyses. We have performed a series of calculations and experiments to demonstrate the potential for constant pressure operation to increase analysis speed for TASF separations. FIG. 11 shows the results of our initial calculations. Panel A demonstrates how flow rate varies with time during a 60 s TASF analysis. Constant flow is shown as a dashed line, constant pressure is plotted as a solid line. Pump maximum pressure, column dimensions, focusing time and temperature and separation temperature were all identical to those in the previous paragraph. Injection volume was set to 1 µL, focusing time was just under 10 s. Following focusing, flow rate increases due to the increase in focusing segment temperature for the constant pressure calculation. The duration of the temperature change between focusing and separation temperatures was set to 7 s. At 53 s focusing segment temperature was reduced to 0° C. to prepare for a subsequent analysis.

It is beneficial to separate samples in fixed, very short analysis times, e.g., two minutes, one minute, 30 s, 15 s. The analysis time depends on solute retention and upon the flow rate(s) during a separation. The effect of these flow rates and their changes on solute retention time can be understood by considering solute retention volume. The retention volume is that volume of mobile phase that must be passed through the column in order to elute a compound with a particular retention factor, k'. If the volume of mobile phase necessary for elution (elution volume) can be delivered in a shorter time then analysis time can be reduced.

Panel B of FIG. 11 demonstrates how analysis time can be reduced by performing TASF separations at constant pressure rather than using constant flow rate. Elution volume (or the volume delivered by the pump) at a given point into the analysis has been plotted for the same hypothetical constant flow (dashed line) and constant pressure TASF (solid line) analyses described above. The dot-dashed line represents a solute with an elution volume of 7.6 µL. At a constant flow rate of 8.3 µL/min this retention volume corresponds to a retention time of 55 s. Operating the pump at constant pressure and increasing mobile phase flow rate after the 10 focusing period to maintain column pressure at 1200 bar this solute can be eluted in 34 s, reducing retention time by 40%. There are clear benefits to operating fast TASF analyses at constant pressure.

FIG. 12 shows an example (experimental) separation of a simple five-component mixture of test solutes under constant flow (top) and constant pressure conditions (bottom). Maximum pump pressure was fixed at 680 bar in both modes. Sample volume was 1 µL of parabens and alkylphenones. The column was a 50 mm long×0.15 mm ID capillary packed with Waters Acquity BEH C18, 1.7 um particles. Separation and focusing segments were packed with 1.7 µm diameter particles. Focusing segment length was 1.0 cm.

The inlet segment was 2.5 cm long and packed with 8 μm diameter solid silica spheres. Detection was absorbance of UV light at 254 nm. Focusing and separation temperatures were 15 and 85° C. Analysis time for the constant flow separation was 100 s. At constant pressure, analysis time was reduced to 75 s, a reduction of 25%. The beneficial result of constant pressure operation was an increase in speed.

Example 6

TASF for Improved Peak Shape

Figure 13:
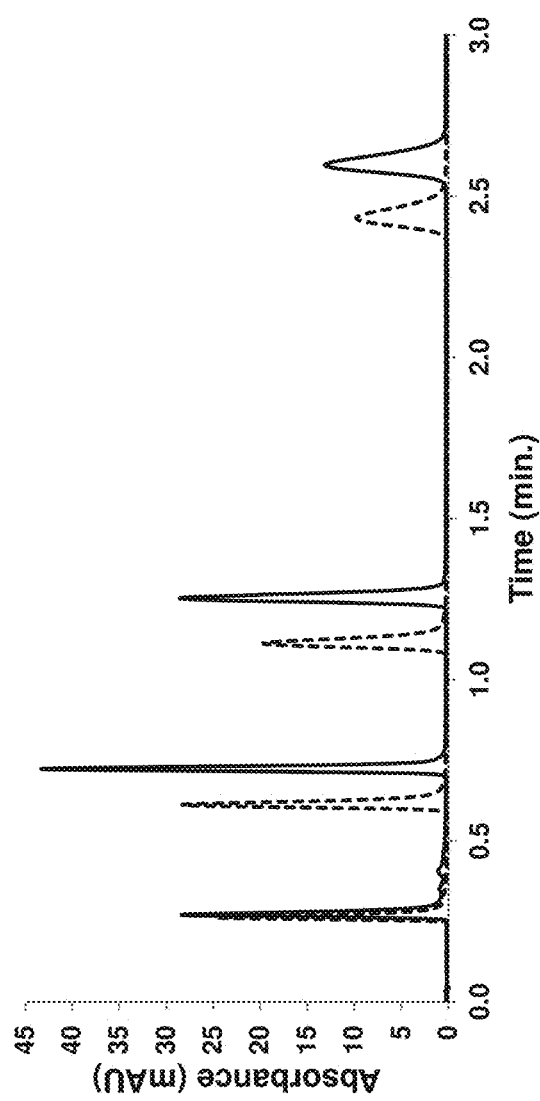
FIG. 13 is a graph depicting the results of TASF for improved peak shape.

Temperature-based focusing improves separation performance by addressing the volume overload problem induced by large volume injections. FIG. 13 shows an application were TASF enhances separation performance for 30 nL injections of uracil and parabens onto the same 47 mm long×0.15 mm ID Waters BEH C18 column used in Example 1. Sample composition and all other TASF and related chromatographic conditions including focusing length were identical to those described in Example 1. Separations under isothermal conditions are in black, TASF are in blue. FIG. 13 shows the 30 nL isothermal injection (dashed line), representing only 7% of the column volume, was not small enough to avoid degrading separation performance relative to a nominally identical 30 nL TASF analysis (solid line). Peak height improvements for all solutes were small, but present in the small volume comparison. In addition peak shape also improved when using TASF, most notably by reducing the size of the so-called peak tail present for the peaks for all retained solutes (parabens). Thus, TASF was also shown to improve separation performance for of small volume samples.

Example 7

Small Molecule Separation in Solvent Gradient Elution Combined with TASF

Figure 14A:
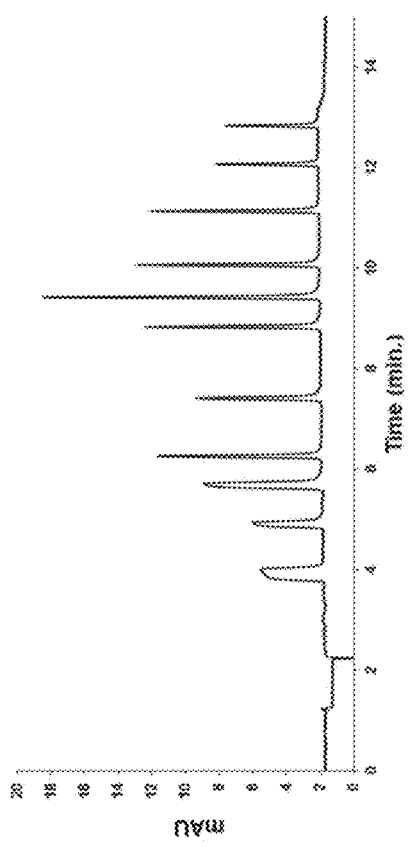
FIGS. 14A and 14B are graphs showing the results of two example separations using the same solvent gradient in which the organic modifier (acetonitrile or solvent "B") composition is changed linearly in time from 5 to 75% B over 12 minutes.
Figure 14B:
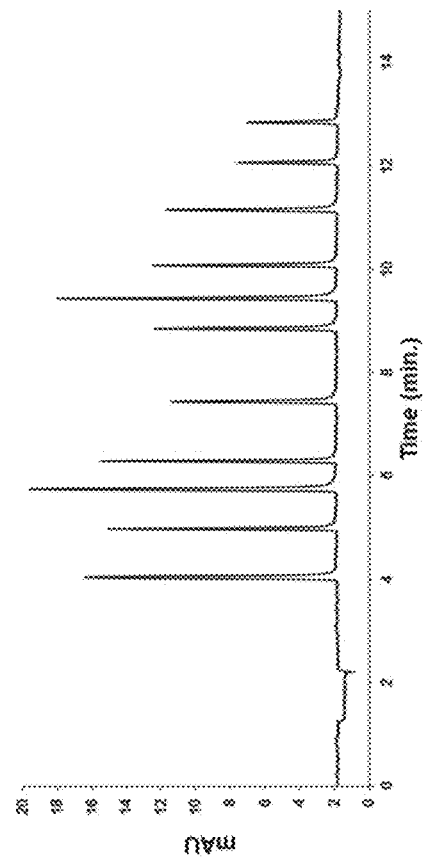

FIGS. 14A and 14B show two example separations using the same solvent gradient in which the organic modifier (acetonitrile or solvent "B") composition is changed linearly in time from 5 to 75 vol % B over 12 minutes. In particular, the solvent program went from 5 vol % acetonitrile/95 vol % water at the start of the run to 75 vol % acetonitrile/25 vol % water at the end of the run. FIG. 14A shows the signal from an isothermal analysis performed at 65° C.; FIG. 14B shows the same separation using TASF and a −7.5° C. focusing temperature. Samples consisted of (in order of elution): acetanilide, acetophenone, methylparaben, propiophenone, ethylparaben, butyrophenone, benzophenone, valerophenone, hexanophenone, heptanopheone and octanophenone. The sample solvent composition was the same as the initial composition of the gradient, 5% B. Column dimensions were 142 mm long×0.10 mm ID. The column was packed with Waters CSH C18, 1.7 μm particles. The focusing segment was 1.0 cm long, the separation segment was 13.2 cm, the inlet segment of the column was packed with 8 μm solid silica spheres. Flow rate was 1.00 μL/min; injection volume was 1000 nL, with a 65 s focusing time. Column volume was 685 nL. Detection was achieved using optical absorbance at 254 nm.

From this example it is important to note the improvements in peak height and shape for each peak in the first half of the chromatogram, up to 8 minutes. When using TASF, satisfactory chromatography resulted. This provided a greater peak capacity for the analysis, an important figure of merit for the analysis. Just as significant, TASF did not adversely influence the quality of the separation for the late eluting solutes. Hence TASF benefited the early eluting solutes without degrading the separation for the late eluting solutes.

Example 8

Peptide Separation in Solvent Gradient Elution Combined with TASF

Figure 15A:
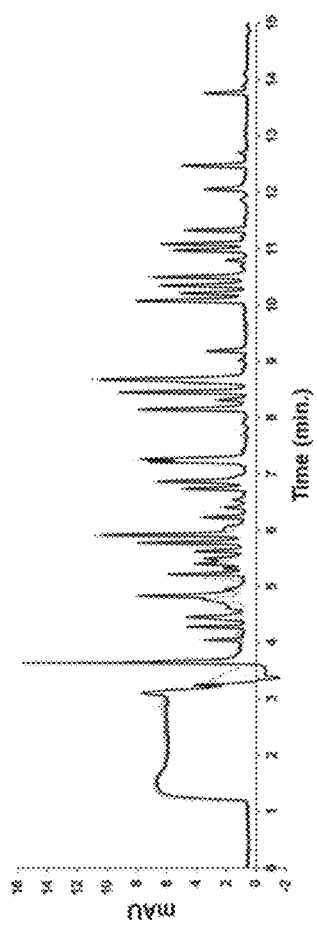
FIGS. 15A and 15B are graphs showing the results of two example separations using the same solvent gradient in which the organic modifier (acetonitrile or solvent "B") composition is changed linearly in time from 5 to 40% B over 12 minutes.
Figure 15B:
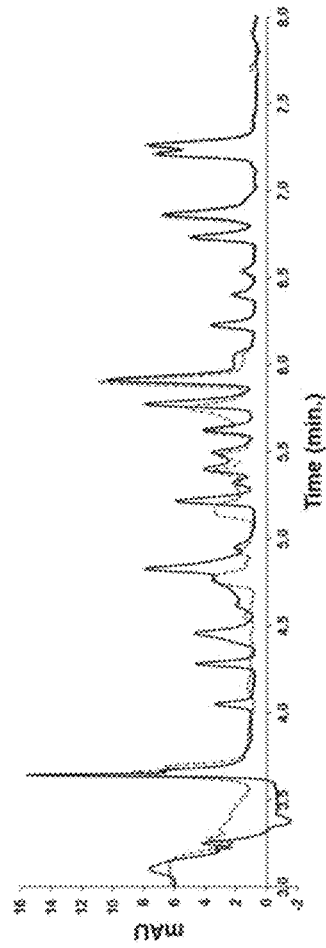

In general the effect of changing mobile phase composition results in a more dramatic change in solute retention for higher molecular weight solutes such as peptides, resulting in greater solvent-based gradient compression. Greater solvent-based gradient compression decreases the effect of volume overload. Thus, in the case of higher molecular weight solutes such as peptides, it might be expected that TASF will not be necessary. To demonstrate the breadth of TASF FIGS. 15A and 15B show its application to a tryptic digest of bovine serum albumin (BSA). In this example a 2000 nL injection of BSA, representing 2.90-times the column volume, was made onto the same column described in the previous example. The sample was prepared in 5% acetonitrile to facilitate dissolution of peptides. The separation utilized a linear gradient from 5-40% acetonitrile over 15 minutes and a flow rate of 1.00 μL/min. Focusing and separation temperatures were, −7.5 (FIG. 15B) and 65° C. (FIG. 15A), respectively. Detection wavelength was 214 nm. With TASF the peak shape of early eluting solutes was significantly improved as was resolution, particularly around the 6-minute mark. Four additional peaks were detected between 3.5 and 4.5 minutes, indicating the potential for TASF to lower concentration detection limits for these peptides.

Example 9

Two-Stage Focusing in Isocratic Elution

Figure 17A:
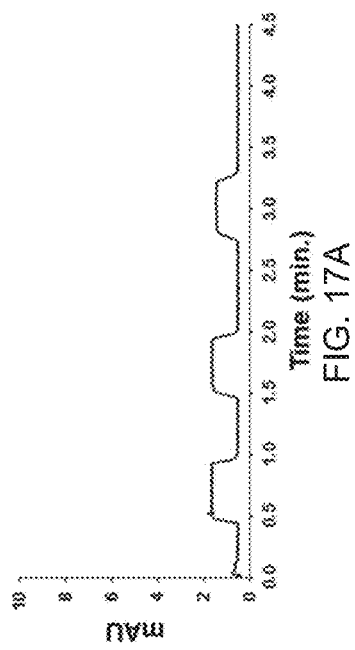
FIGS. 17A, 17B and 17C are chromatograms resulting from 1500 nL injections of uracil, ethylparaben and propylparaben under isothermal (comparative example) (FIG. 17A), one-stage temperature-based focusing (FIG. 17B) and two-stage temperature-based focusing (FIG. 17C) conditions.
Figure 17B:
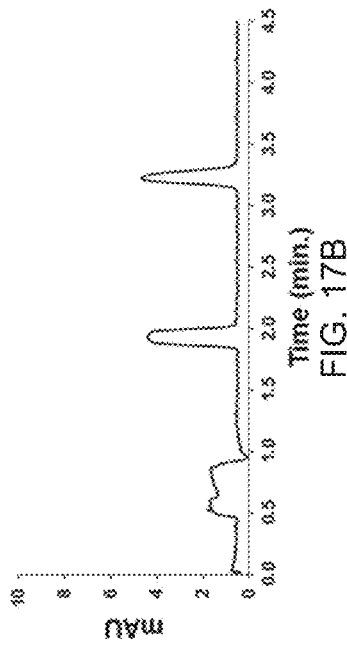
Figure 17C:
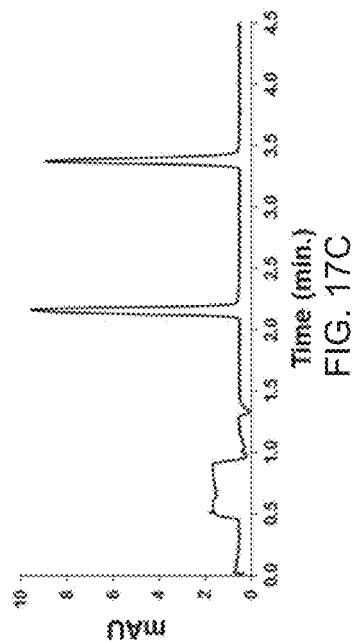

FIGS. 17A, 17B and 17C show chromatograms resulting from 1500 nL injections of uracil, ethylparaben and propylparaben under isothermal (FIG. 17A), TASF (FIG. 17B) and two-stage TASF (FIG. 17C) conditions. Column dimensions were 78 mm long×0.15 mm ID; it was packed with Waters BEH C18, 1.7 μm particles. Each focusing segment was 1.0 cm long, the separation segment (5.8 cm) was packed with the same particles. The inlet segment was 2.5 cm long and packed with 8 μm diameter solid silica spheres. Column volume was estimated to be 750 nL, sample volume was 2.00-times the column volume. Sample solvent composition was the same as the mobile phase. Mobile phase composition was 80:20 water/acetonitrile. Flow rate was 3 μL/min. Focusing and separation temperatures were 5 and 70° C. In FIG. 17A there was no TASF: the temperatures of 4a, 4b and 6 were held at 70° C. throughout the run. In FIG. 17B, there was single-stage TASF: the temperatures of 4a and 4b were held at 5° C. for 35 s prior to being raised to 70° C. In FIG. 17C, there was two-stage TASF: 4a was held at 5° C. for 35 s and then raised to 70° C. TEC 4b was at 5° C. for 60 s prior to being raised to 70° C. Detection was by optical absorbance at 254 nm. For this separation single-stage TASF (FIG. 17B) increased ethylparaben (2) and propylparaben (3) peak height compared to the isothermal separation (FIG. 17A) by a factor of 3.4 and 4.3 and decreased peak width by a factor of 3.6 and 4.6. Benefits of two-stage TASF (FIG. 17C) are visible when comparing it to the TASF separation (FIG. 17B). For ethylparaben (2) two-stage TASF increased peak height by an additional factor of 2.3 and decreased peak width by a factor of 2.4 compared to the TASF separation. The propylparaben peak (3) was also improved. Peak height increased by a factor of 2.0 and peak width decreased by a factor of 2.2. The uracil peak is unaffected because it is not retained and thus cannot be focused. In this example the advantage to using two-stage TASF relative to TASF (single focusing segment) is apparent, the second focusing stage induced additional focusing.

Example 10

Two-stage Focusing in Gradient Elution

Figure 18A:
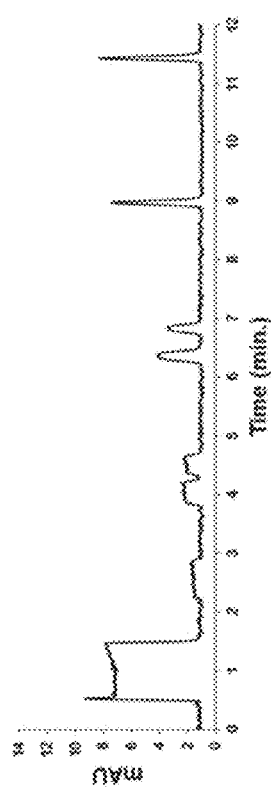
FIGS. 18A, 18B and 18C are chromatograms resulting from 3000 nL injections of uracil, methylparaben, ethylparaben, n-propylparaben, n-butylparaben, p-hydroxyacetophenone, p-hydroxypropiophenone and p-hydroxybutyrophenone under isothermal (comparative example) (FIG. 18A), one-stage temperature-based focusing (FIG. 18B) and two-stage temperature-based focusing (FIG. 18C) conditions.
Figure 18B:
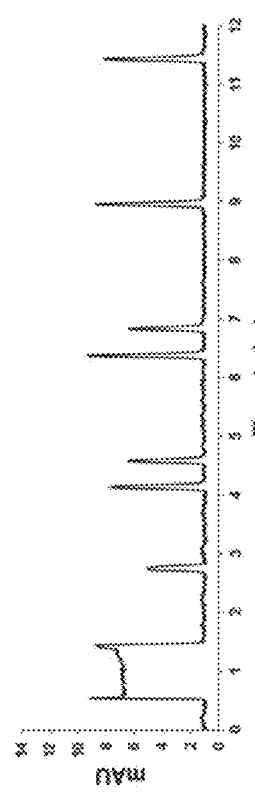
Figure 18C:
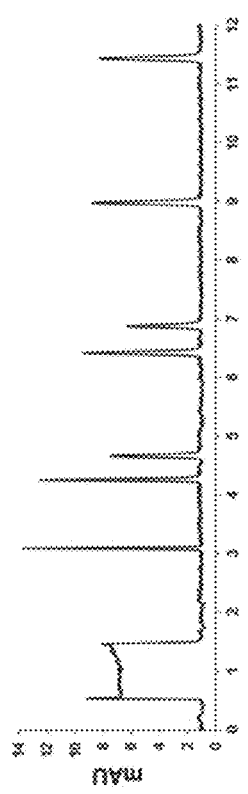
Figure 19:
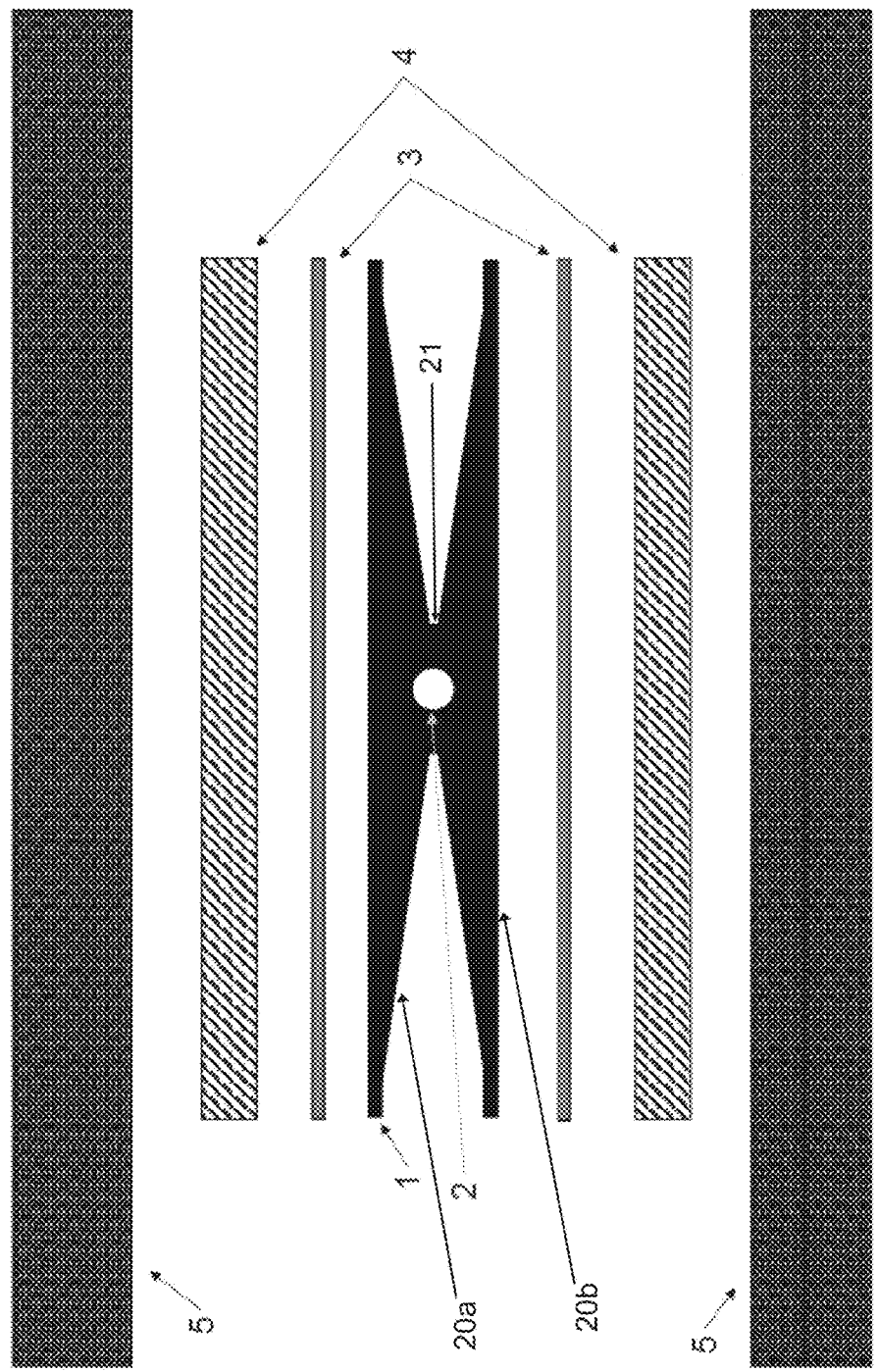
FIG. 19 is a cross-section exploded view of a precolumn as disclosed herein.
Figure 20:
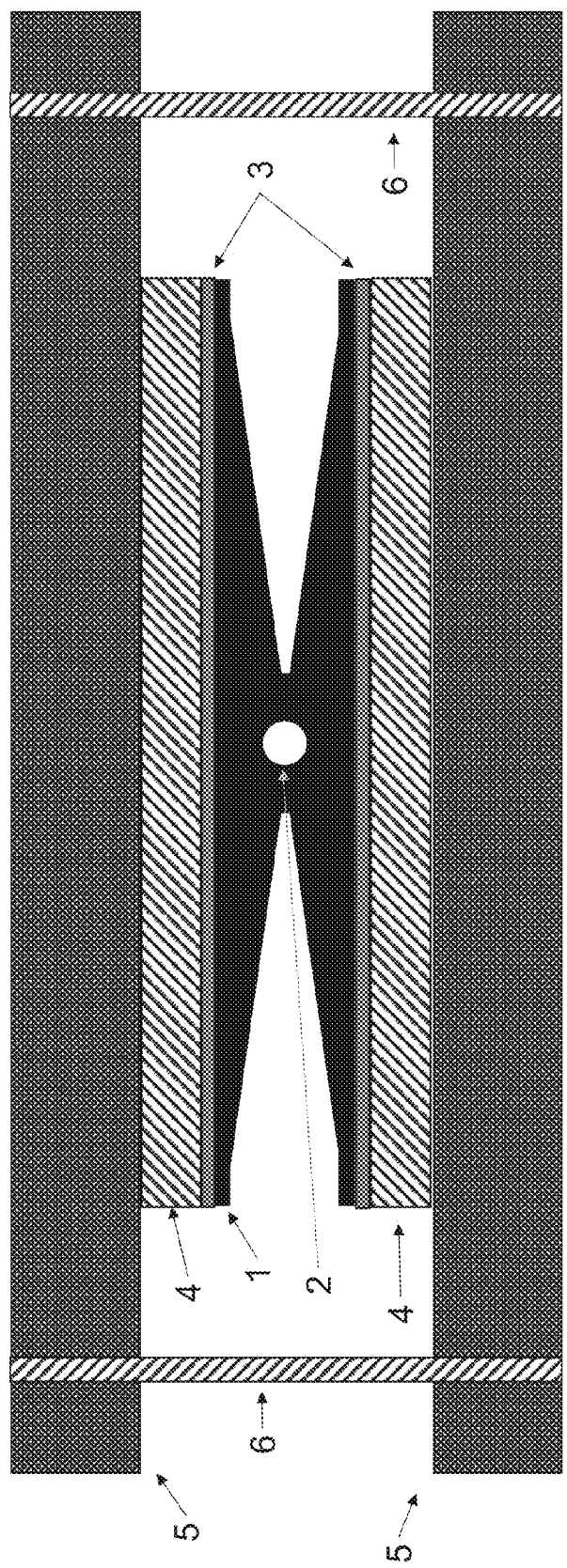
FIG. 20 is a cross-section view of a precolumn assembly as disclosed herein.
Figure 21:
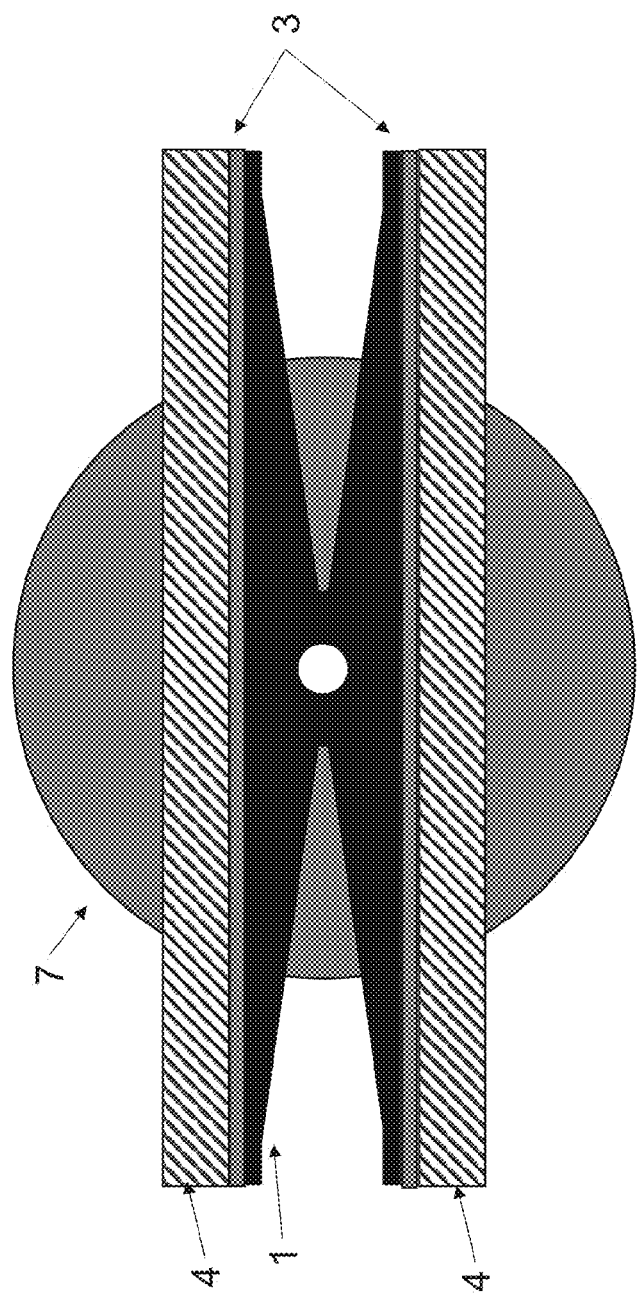
FIG. 21 is a cross-section view of a precolumn with an end fitting as disclosed herein.
Figure 22:
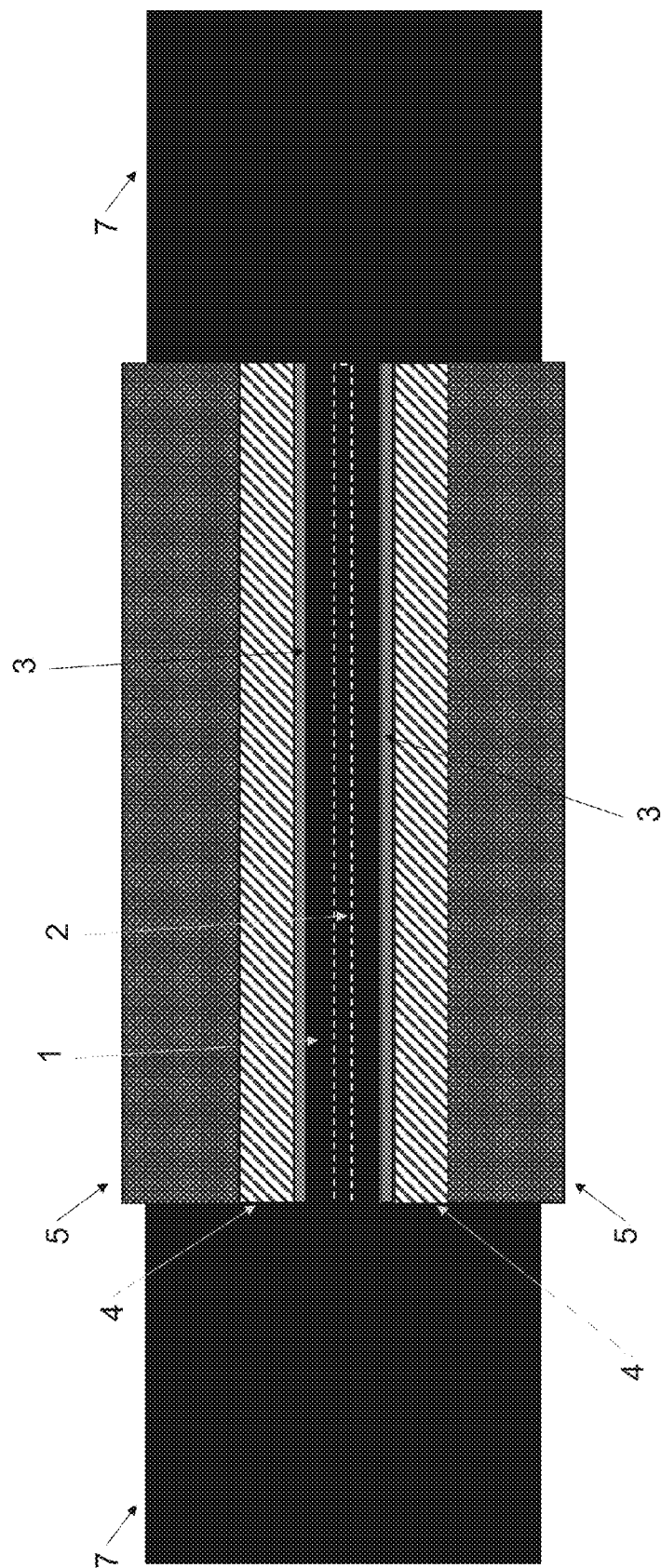
FIG. 22 is a cross-section longitudinal axis view of a precolumn as disclosed herein.

FIGS. 18A, 18B and 18C illustrate the application of two-stage TASF to gradient elution. The isothermal separation is FIG. 18A, single-stage TASF is FIG. 18B and two-stage TASF is FIG. 18C. In this example a series of seven retained solutes and the unretained uracil were injected onto the same column described in the previous example. Solutes were (in order of elution): uracil, p-hydroxyacetophenone, methylparaben, p-hydroxypropiophenone, ethylparaben, p-hydroxybutyrophenone, n-propylparaben and n-butylparaben. Injection volume was 3000 nL, equivalent to 4.00-times the column fluid volume. The linear gradient was from 5-45% B in 16 minutes. The A channel of the pump was water; B was acetonitrile. Sample solvents were the same as the initial composition of the gradient, 5% B. Flow rate was 3.00 µL/min, detection was by optical absorbance at 254 nm. FIG. 18A shows the gradient chromatogram in the absence of TASF: all TECs and the column temperature were 70° C. TASF was used for the chromatograms shown in FIGS. 18B (single-stage TASF) and 18C (two-stage TASF). TEC 4a was held at 5° C. for 65 s for the chromatograms shown in both FIGS. 18B and 18C. Focusing times for TEC 4b, during which it was at 5° C., were 65 s for the chromatogram in FIG. 18B and 100 s for FIG. 18C. Chromatographic performance was improved relative to the isothermal separation for each solute by using single-stage ASF (FIG. 18B). The improvement was better for two-stage TASF (FIG. 18C). For the most hydrophilic solute, p-hydroxyacetophenone, two-stage TASF increased detectability (peak height) by a factor of 3.1 relative to TASF. Similar benefits, while smaller in magnitude, for the more hydrophobic solutes in this example were also obtained by moving from TASF to two-stage TASF. Two-stage is useful for large volume samples separated using solvent gradient elution. Two-stage TASF can be used to improve peak capacity over single-stage TASF or over isothermal separations by gradient elution.

Example 11

TASF for Large Diameter Columns, Heat Transfer Simulations

Figure 24:
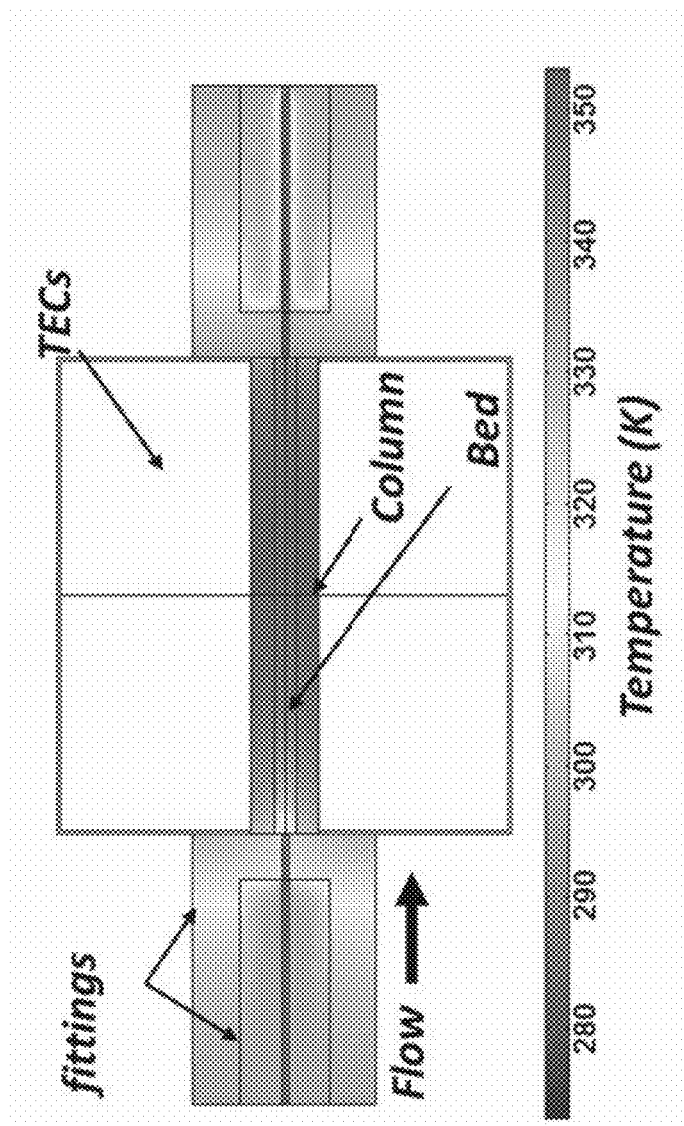
FIG. 24 shows a temperature profile in a precolumn as disclosed herein.

COMSOL numerical calculations have been carried out for a 20×1.0 mm ID precolumn with a packed bed, aqueous mobile phase and stationary phase with total porosity equal to 0.6. This embodiment of TASF has been designed for use with 2.1 mm ID separation columns. A typical flow rate for a 2.1 mm ID×50 mm long column is 0.50 mL/min ($t_0$=12 s) which corresponds to a $t_0$ in the precolumn of 1.1 s. FIG. 24 shows the temperature profile in the system at the midline of the column (along the z-axis). The incoming fluid is at 298 K, and the precolumn was at 273 K prior to reversing the current to achieve a release temperature of 353 K. The temperature profile shown is 3.5 s after TEC current was reversed. Note that the simulation shows the radial velocity inhomogeneity described above during the heating phase. Radial velocity inhomogeneities degrade the performance of the downstream separation. For a low retention solute, k'=2, the contribution to bandspreading time standard deviation due to the velocity inhomogeneity that occurs during the entire process of release is 33 ms, clearly an inconsequential time compared to even the smallest achievable peak widths.

Example 12

TASF for Large Diameter Columns

In this example a temperature-controlled precolumn packed with C18 stationary phase particles is placed before a commercial 50×2.1 mm ID column. To ensure focusing, the leading edge of the injected band of solute must not elute from the precolumn during sample loading. The 1.0 mm ID precolumn must be compatible with 2.1 mm ID columns, e.g. at 0.5 mL/min. For the 20 mm long device an injection volume of 100 µL (equal to the fluid volume of the 50×2.1 mm ID column) is targeted. Solutes in this injected volume must have a k' of 10 or greater to be confined to the precolumn during the injection time, 12 s at a flow rate of 0.5 mL/min. Based on previously collected retention data for methylparaben and acetophenone the conditions under which the solute would just reach the end of the precolumn are shown in the table below.

|  | T required/° C. | |
| --- | --- | --- |
| Φ | Methylparaben | Acetophenone |
| 0.1 | >25 | >25 |
| 0.15 | 22 | >25 |
| 0.20 | −1 | 16 |
| 0.25 | — | 6 |

For example, when the sample contains 20% acetonitrile, a focusing temperature of −1° C. would be needed for methylparaben and 16° C. for acetophenone. For a sample in 10% acetonitrile, focusing will occur near room temperature from the solvent alone. Temperatures below −15° C. are achievable depending on the solvent composition, but currently it is not preferable to use lower temperatures because of the nuisance created by condensation. Use of longer precolumns would be easy to make and represent a simple solution to the need to use colder focusing temperatures. Added length relaxes the conditions of sample composition and temperature required to focus the target injection volume or could be used to focus larger volumes with the same criteria.

Any stationary phase, i.e. packed particles, monoliths, etc., would work for the stationary phase of the precolumn. The effect of temperature also does not need to be known. Experimental conditions leading to effective focusing are easily determined by determining the maximum volume injected (at a given solvent composition for the sample being injected) at two temperature and use of the van't Hoff relationship to interpolate or extrapolate to other temperature.

In view of the many possible embodiments to which the principles of the disclosed invention may be applied, it should be recognized that the illustrated embodiments are only preferred examples of the invention and should not be taken as limiting the scope of the invention.

What is claimed is:

1. A device comprising:
a liquid chromatography column having a longitudinal length and including a sample introduction inlet, an outlet, a longitudinally-extending inlet segment having a first end and a second end, a longitudinally-extending focusing segment having a first end and a second end, and a longitudinally-extending separation segment having a first end a second end, wherein the first end of the inlet segment is longitudinally adjacent to the sample introduction inlet of the liquid chromatography column, the second end of the inlet segment is longitudinally adjacent to the first end of the focusing segment, the second end of the focusing segment is longitudinally adjacent to the first end of the separation segment, and the second end of the separation segment is longitudinally adjacent to the outlet of the liquid chromatography column, and wherein the inlet segment contains noninteracting, nonporous silica spheres and the focusing segment and the separation segment both contain particles that have a surface chemistry that is different than the noninteracting, nonporous silica spheres contained in the inlet segment;
at least one Peltier thermoelectric cooling element aligned along the focusing segment; and
a resistive heater aligned along the separation segment.

2. The device of claim 1, wherein the focusing segment has a longitudinally-extending length that is 1 percent to 50 percent of the total length of the sum of the focusing segment longitudinally-extending length and the separation segment longitudinally extending length.

3. The device of claim 1, wherein the liquid chromatography column is a capillary liquid chromatography column.

4. The device of claim 1, wherein the particles contained in the focusing segment have an average particle diameter that is larger than the average particle diameter of the particles contained in the separation segment.

5. The device of claim 1, wherein the device further comprises a sample injection element adjacent to the sample introduction inlet of the liquid chromatography column.

6. The device of claim 1, wherein the device includes at least two focusing segments.

7. The device of claim 1, wherein the focusing segment has a longitudinally-extending length that is 3 percent to 35 percent of the total length of the sum of the focusing segment longitudinally-extending length and the separation segment longitudinally-extending length.

8. The device of claim 1, wherein the focusing segment has a longitudinally-extending length that is 5 percent to 20 percent of the total length of the sum of the focusing segment longitudinally-extending length and the separation segment longitudinally-extending length.

9. The device of claim 2, wherein the particles contained in the focusing segment have an average particle diameter that is larger than the average particle diameter of the particles contained in the separation segment.

10. The device of claim 1, wherein a Peltier thermoelectric cooling element is not aligned along the separation segment.

11. The device of claim 1, wherein the particles contained in the focusing segment have a particle diameter of 1.5 µm to 10 µm, and the particles contained in the separation segment have a particle diameter of 1.0 µm to 5 µm.

12. The device of claim 1, wherein the particles contained in the focusing segment have a particle diameter and the particles contained in the separation segment have a particle diameter, wherein the focusing segment particle diameters are at least equal in size but no more than four times greater than the separation segment particle diameters.

13. The device of claim 1, wherein the particles contained in the focusing segment and the separation segment are stationary phase particles.

14. The device of claim 11, wherein the particles contained in the focusing segment are stationary phase particles and the particles contained in the separation segment are stationary phase particles.

15. The device of claim 12, wherein the particles contained in the focusing segment are stationary phase particles and the particles contained in the separation segment are stationary phase particles.

16. The device of claim 1, wherein the particles contained in the focusing segment have the same surface chemistry as the particles contained in the separation segment.

17. The device of claim 1, wherein the particles contained in the focusing segment have a different surface chemistry compared to the particles contained in the separation segment.

* * * * *